(12) United States Patent
Izadpanah et al.

(10) Patent No.: US 9,447,379 B2
(45) Date of Patent: Sep. 20, 2016

(54) DERIVATION OF HEMATOPOIETIC CELLS FROM ADULT MESENCHYMAL STEM CELLS

(76) Inventors: Reza Izadpanah, Mandeville, LA (US); Eckhard Alt, Houston, TX (US)

( * ) Notice: Subject to any disclaimer, the term of this patent is extended or adjusted under 35 U.S.C. 154(b) by 393 days.

(21) Appl. No.: 13/581,432

(22) PCT Filed: Feb. 28, 2011

(86) PCT No.: PCT/US2011/026486
§ 371 (c)(1),
(2), (4) Date: Apr. 10, 2013

(87) PCT Pub. No.: WO2011/106775
PCT Pub. Date: Sep. 1, 2011

(65) Prior Publication Data
US 2013/0190729 A1 Jul. 25, 2013

Related U.S. Application Data

(60) Provisional application No. 61/308,931, filed on Feb. 27, 2010.

(51) Int. Cl.
| | | |
|---|---|---|
| *C12N 5/078* | (2010.01) |
| *C12N 5/0786* | (2010.01) |
| *C12N 5/0784* | (2010.01) |
| *C12N 5/0787* | (2010.01) |
| *C12N 5/0789* | (2010.01) |
| *C12N 5/0793* | (2010.01) |
| *C12N 15/85* | (2006.01) |
| *C12N 15/88* | (2006.01) |
| *C12Q 1/68* | (2006.01) |

(52) U.S. Cl.
CPC ............ *C12N 5/0647* (2013.01); *C12N 5/0619* (2013.01); *C12N 5/0639* (2013.01); *C12N 5/0642* (2013.01); *C12N 5/0645* (2013.01); *C12N 15/85* (2013.01); *C12N 15/88* (2013.01); *C12Q 1/6886* (2013.01); *C12N 2501/22* (2013.01); *C12N 2501/2303* (2013.01); *C12N 2506/1384* (2013.01)

(58) Field of Classification Search
None
See application file for complete search history.

(56) References Cited

U.S. PATENT DOCUMENTS

| | | | |
|---|---|---|---|
| 5,199,942 A | 4/1993 | Gillis | |
| 5,599,705 A * | 2/1997 | Cameron | 435/378 |
| 6,037,174 A | 3/2000 | Smith et al. | |
| 6,991,787 B1 | 1/2006 | Greenberger et al. | |
| 7,078,230 B2 | 7/2006 | Wilkison et al. | |
| 2004/0067218 A1 | 4/2004 | Casteilla et al. | |
| 2010/0310527 A1 | 12/2010 | Alt et al. | |

FOREIGN PATENT DOCUMENTS

| | | |
|---|---|---|
| WO | 03/080801 A2 | 10/2003 |
| WO | 2007/136424 A2 | 11/2007 |

OTHER PUBLICATIONS

Hans et al, Blood, 2010, vol. 115, No. 5, pp. 957-964.*
Lardon et al, Immunology, 1997, vol. 91, pp. 553-559.*
Fang et al, Archives of Medical Research, 2009, vol. 40, pp. 311-317.*
Bonnet, D & Dick JE "Human Acute myeloid leukemia is organized as a hierarchy that originated from a primitive hematopoietic cell" Nature Medicine vol. 3 (7) (1997) pp. 730-737.
Choi K-D et al "Generation of mature human myelomonocytic cells through expansion and differentiation of pluripotent stem cell-derived lin-CH34+CH43+CD45+ progenitors" Journal Clinical Investigation 119(9) (2009) pp. 2818-2829.
Cousin B et al. "Reconstitution of lethally irradiated mice by cells isolated from adipose tissue" Biochemical and Biophysical Research Communications 301 (2003) pp. 1016-1022.
Freisinger, E. et al, "Characterization of hematopoietic potential of mesenchymal stem cells", Journal of Cellular Physiology, vol. 225 (2010) pp. 888-897.
Gratwohl A, et al. "Autologous hematopoietic stem cell transplantation for autoimmune diseases" Bone Marrow Transplantation 35 (2005) pp. 869-879.
Han J et al. "Adipose tissue is an extramedulary reservoir for functional hematopoietic stem and progenitor cells" Blood 115 (2010) pp. 957-964.
Izadpanah, R et al "Long-term in vitro expansion alters the biology of adult mesenchymal stem cells" Cancer Res. 68 (11) (2008) 4229-4238.
Karlsson KR et al "Homogeneous monocytes and macrophages from human embryonic stem cells following coculture-free differentiation in M-CSF and IL-3" Experimental Hematology 36 (2008) pp. 1167-1175.
Lieber JG et al "The in vitro production and characterization of neutrophils from embryonic stem cells" Blood 103 (2004) pp. 852-859.
Marappagoundar, D "Characterization of Human Adipose Tissue Derived Hematopoietic Stem Cell, Mesenchymal Stem Cell and Side Population Cells" Int'l J of Biology vol. 2 (1) (2010) 71-78.
Minana M-D, et al. "IFATS Collection: Identification of Hemangioblasts in the Adult Human Adipose Tissue" Stem Cells 26 (2008) 2696-2704.
Prunet-Marcassus B et al: "From heterogeneity to plasticity in adipose tissues: Site-specific differences" Experimental Cell Research, vol. 312 (6) (2006) pp. 727-736.
Poglio S. et al. "Adipose Tissue as a Dedicated Reservoir of Functional Mast Cell Progenitors" Stem Cells 28 (2010) 2065-2072.
Regenerative Medicine 2006, publication of the NIH, available for download at http://stemcells.nih.gov/staticresources/info/scireport/PDFs/Regenerative_Medicine_2006.pdf.

(Continued)

*Primary Examiner* — Allison Fox
(74) *Attorney, Agent, or Firm* — Blank Rome LLP

(57) ABSTRACT

Methods and compositions for differentiating tissue resident multipotent mesenchmal stromal cells (MSCs) such as adipose tissue resident MSCs into a hematopoietic lineage are described.

17 Claims, 9 Drawing Sheets

(56) References Cited

OTHER PUBLICATIONS

Schaffler, A. and Buehler, C "Concise Review: Adipose Tissue-Derived Stromal Cells—Basic and Clinical Implications for Novel Cell-Based Therapies" Stem Cells 25 (2007) 818-827.

Schenk M et al "IL-1beta triggers monocytes to differentiate into CD209+ macrophages" FASEB J vol. 22 (1) Apr. 2008 Meeting abstract Ib539.

Vodyanik MA et al "Human embryonic stem cell-derived CD34+ cells: efficient production in the coculture with OP9 stromal cells and analysis of lymphohematopoietic potential" Blood. 105 (2005) 617-626.

Zheng, B. et al, "Mouse adipose-derived stem cells undergo multilineage differentiation in vitro but primarily osteogenic and chondrogenic differentiation in vivo" Tissue Engineering, vol. 12 (2006) pp. 1891-1901.

Anderson JS, et al. Derivation of normal macrophages from human embryonic stem (hES) cells for applications in HIV gene therapy. Retrovirology vol. 3 (2006) 24 (11pgs).

Crippa, F. et al "Infectious Complications after Autologous CD34-Selected Peripheral Blood Stem Cell Transplantation" Biology of Blood and Marrow Transplantation vol. 8 (2002) 281-289.

Dominici M, et al "Minimal criteria for defining multipotent mesenchymal stromal cells" Cytotherapy. vol. 8(4) (2006) 315-7.

Gordon S, Taylor PR. Monocyte and macrophage heterogeneity. Nat Rev Immunol. vol. 5(12) (2005) 953-64.

Heusohn F et al "Coordinate Expression of the Lineage-specific Growth Factor Colony-Stimulating Factor (CSF)-1 and Its Receptor Selectively Promotes Macrophage Maturation during Differentiation of Multipotential Progenitor Cells" Cell Growth & Differentiation vol. 5 (1994) 1119-1126.

Hino M. et al "Ex vivo expansion of mature human neutrophils with normal functions from purified peripheral blood CD341 haematopoietic progenitor cells" British Journal of Haematology, vol. 109 (2000) 314-321.

Izadpanah R et al. "Biologic Properties of Mesenchymal Stem Cells Derived From Bone Marrow and Adipose Tissue" J Cell Biochem. vol. 99(5) (2006) 1285-1297.

Izadpanah R et al. "Characterization of Multipotent Mesenchymal Stem Cells from the Bone Marrow of Rhesus Macaques" Stem Cells and Development vol. 14 (2005) 440-451.

Katz AJ, et al. Emerging approaches to the tissue engineering of fat. Clin Plast Surg. vol. 26(4) (1999) 587-603.

Kilroy GE et al "Cytokine Profile of Human Adipose-Derived Stem Cells: Expression of Angiogenic, Hematopoietic, and Pro-Inflammatory Factors" J. Cell. Physiol. 212 (2007) 702-709.

Long, Xiaoxiao, et al. "Neural Cell Differentiation In Vitro from Adult Human Bone Marrow Mesenchymal Stem Cells" Stem Cells and Development. vol. 14(1) (2005) 65-69.

Mitchell PLR et al "Peripheral blood stem cells used to augment autologous bone marrow transplantation" Archives of Disease in Childhood vol. 70 (1994) 237-240.

Moore KJ et al "In Vitro—Differentiated Embryonic Stem Cell Macrophages a Model System for Studying Atherosclerosis-Associated Macrophage Functions" Arterioscler Thromb Vasc Biol. 1vol. 8(1998) 1647-1654.

Prockop DJ. "Marrow stromal cells as stem cells for nonhematopoietic tissues" Science 276 (1997) 71-74.

Ratajczak MZ, et al. "The c-kit proto-oncogene in normal and malignant human hematopoiesis" Int J Cell Cloning vol. 10 (1992) 205-214.

Rodbell M "Metabolism of Isolated Fat Cells" J. Biol Chem. 239 (2) (1964) 375-380.

Safford, KM, et al "Neurogenic differentiation of murine and human adipose-derived stromal cells" Biochemical and Biophysical Research Communications vol. 294 (2) (2002) pp. 371-379.

Schimrosczyk K et al "Liposome-mediated transfection with extract from neonatal rat cardiomyocytes induces transdifferentiation of human adipose-derived stem cells into cardiomyocytes" The Scandinavian Journal of Clinical & Laboratory Investigation, 2008, iFirst Article, 1-9.

Zuk P A, et al. "Multilineage cells from human adipose tissue: implications for cell based therapies" Tissue Eng. vol. 7 (2001) 211-228.

\* cited by examiner

| RT-PCR Primers | Sequence Forward | Sequence Reverse | Expected Band Size | Tm |
|---|---|---|---|---|
| GAPDH | 5'-CGAGATCCCTCCAAAATCAA-3' | 5'-GGTGCTAAGCAGTTGGTGGT-3' | 239 bp | 60°C |
| CD4 | 5'-CTCCCCACTGCTCATTTGGAT-3' | 5'-AACAGTCCCATGCTCCATGCT-3' | 102 bp | 60°C |
| CD8 | 5'-TTCGGGGAGATACGTCTAACCCTGTGC-3' | 5'-TTTAGCCTCCCCCTTGTAAAACGGGCG-3' | 379 bp | 60°C |
| CD14 | 5'-GCCCTTACCAGCCTAGACCT-3' | 5'-CCCGTCCAGTGTCAGGTTAT-3' | 404 bp | 60°C |
| CD32 | 5'-CCTCACCTGGAGTTCCAGGAGGGAG-3' | 5'-TAGATCAAGGCCACTACAGCAGCAA-3' | 334 bp | 60°C |
| CD64 | 5'-ACACCACAAGGCAGTGA-3' | 5'-CACCCAGAGAACAGTGTT-3' | 881 bp | 60°C |
| CD68 | 5'-GCTACATGGCGGTGGAGTACAA-3' | 5'-ATGATGAGAGGCAGCAAGATGG-3' | 263 bp | 60°C |
| CCR5 | 5'-CAAAAGAAGGTCTCATTACACC-3' | 5'-CCTGTGCCTCTTCTCTCATTCG-3' | 189 bp | 60°C |
| CSFR1 | 5'-GCCTGTCTCCACTTCTTCAA-3' | 5'-GGTATCCATCCTTCACCAGT-3' | 440 bp | 55°C |
| IFNGR1 | 5'-GGCAGCATCGCTTTAAACTC-3' | 5'-GGAGGTGGGGCTTTTATTA-3' | 195 bp | 60°C |
| MCP-1 | 5'-CAGCCAGATGCAATCAATGC-3' | 5'-GTGGTCCATGGAATCCTGAA-3' | 198 bp | 60°C |
| MRC1 | 5'-TGGTTTCATTGAAAGTGCTGC-3' | 5'-TTCCTGGGCTTGACTGTTTA-3' | 504 bp | 55°C |

Primers were Purchased from Invitrogen real-time RT-PCR

FIG. 5A

| | Sequence Forward | Sequence Reverse | Expected Band Size | Tm |
|---|---|---|---|---|
| GAPDH[1] | 5'-GAA GGT GAA GGT CGG AGT C-3' | 5'-GAA GAT GGT GAT GGG ATT TC-3' | 226bp | |
| Hematopoietic Markers | | | | |
| c-KIT[2] | 5'-CCG TGG TAG ACC ATT CTG TG-3' | 5'-GTG CCC ACT ATC CTG GAG TT-3' | 195 bp | 59°C |
| PROM1[2] | 5'-CCT CTG GTG GGG TAT TTC TT-3' | 5'-CAG TTT CCG ACT CCT TTT GA-3' | 210 bp | 59°C |
| CD4[2] | 5'-GTA GTA GCC CCT CAG TGC AA-3' | 5'-AAA GCT AGC ACC ACG ATG TC-3' | 169 bp | 58°C |
| Unspecific Macrophage/Monocyte Differentiation Markers | | | | |
| CCR5[1] | 5'-CAA AAA GAA GGT CTT CAT TAC ACC-3' | 5'-CCT GTG CCT CTT CTT CTC ATT TCG-3' | 189 bp | 60°C |
| TNF[2] | 5'-TCC TTC AGA CAC CCT CAA CC-3' | 5'-AGG CCC CAG TTT GAA TTC TT-3' | 173 bp | 60°C |
| IL-10[2] | 5'-AAG CCT GAC CAC GCT TTC TA-3' | 5'-ATG AAG TGG TTG GGG AAT GA-3' | 193 bp | 60°C |
| HLADR B1[2] | 5'-CTG GTG ATG CTG GAA ATG AC-3' | 5'-CAG AAG CCC TTT CTG ACT CC-3' | 213 bp | 59°C |
| CD14[2] | 5'-ACA GGA CTT GCA CTT TCC AG-3' | 5'-TCC AGG ATT GTC AGA CAG GT-3' | 201 bp | 58°C |
| Specific Macrophage/Monocyte Differentiation Markers | | | | |
| CD68[2] | 5'-CAA CTG CCA CTC ACA GTC CT-3' | 5'-CAA TGG TCT CCT TGG AGG TT-3' | 159 bp | 59°C |
| CD11b[2] | 5'-ACG GAT GGA GAA AAG TTT GG-3' | 5'-CAA AGA TCT CCC GAA GC-3' | 232 bp | 59°C |
| MRC1[2] | 5'-GGC GGT GAC CTC ACA AGT AT-3' | 5'-ACG AAG CCA TTT GGT AAA CG-3' | 163 bp | 60°C |

Primers were Purchased from Invitrogen[1] and Realtimeprimers.com[2]

FIG. 5B

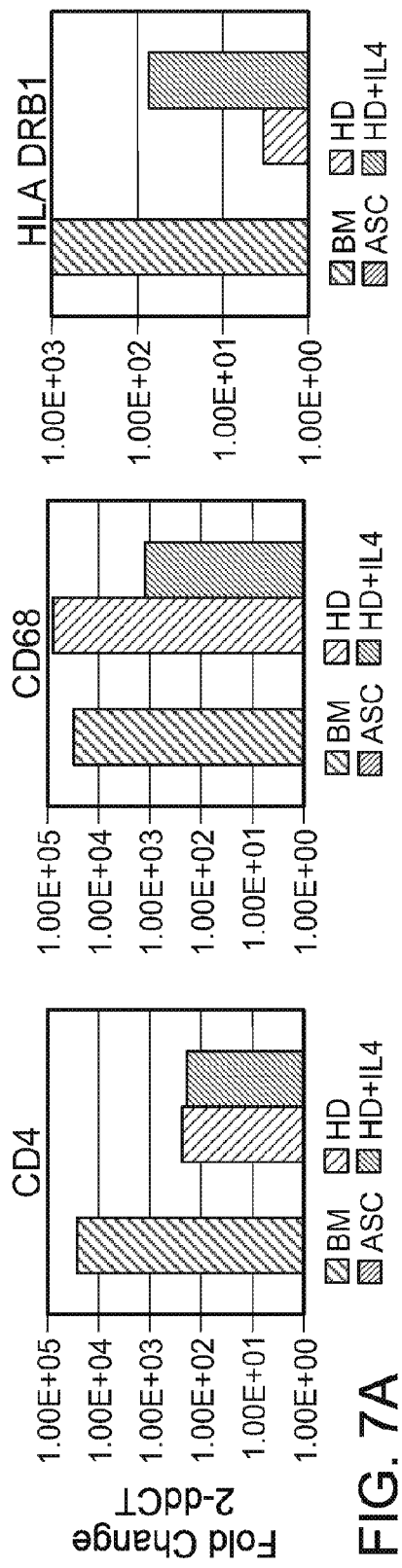
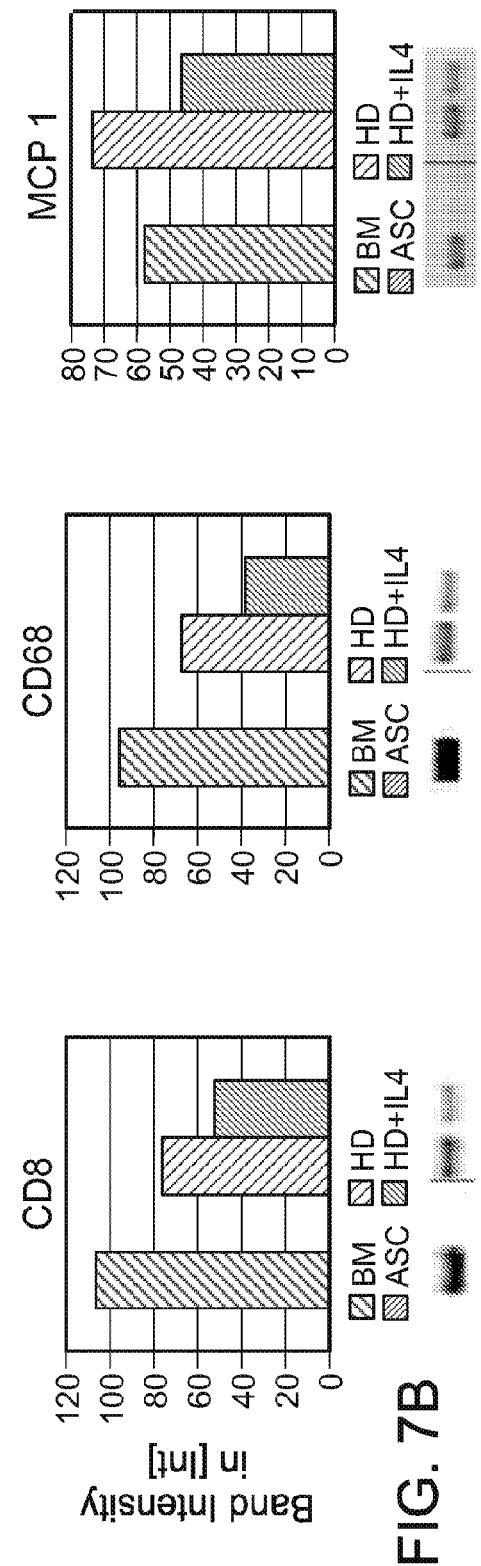
FIG. 7A
FIG. 7B

DERIVATION OF HEMATOPOIETIC CELLS FROM ADULT MESENCHYMAL STEM CELLS

CROSS REFERENCE TO RELATED APPLICATION

This is a U.S. National Phase Application under 37 U.S.C. 0 371 of International Application No. PCT/US2011/026486, filed Feb. 28, 2011, and claims priority to U.S. Provisional Application No. 61/308,931, filed Feb. 27, 2010. The contents of the foregoing applications are hereby incorporated by reference in their entirety. The International Patent Application was published in English on Sep. 1, 2011, as WO 2011/106775 A2.

FIELD OF THE INVENTION

This invention relates generally to cell therapy and the generation and use of stem cells for cell therapy interventions.

BACKGROUND OF THE INVENTION

Without limiting the scope of the invention, its background is described in connection with historical sources of cells of hematopoietic lineage for cell therapy. Cell therapy is utilized for the treatment of a number of diseases including inborn errors and acquired malignancies. The classical source for cell therapy has been bone marrow although there has been some use of umbilical stem cells and peripheral stem cells isolated by apheresis, which are increasingly being used in lieu of bone marrow.

Mesenchymal stromal (a.k.a. stem) cells (MSC) and hematopoietic stem cells (HSCs) have been identified as two main sources of adult stem cells. MSCs have been described as tissue resident adult multipotent cells that develop from embryonic mesodermal germ layer. MSCs have a high capacity of self-renewal while maintaining their multipotent differentiation potential. MSCs are known to develop into cells of mesodermal origin such as adipocytes, osteocytes, chondrocytes, hepatocytes, and myocytes. See Prockop D J. "Marrow stromal cells as stem cells for nonhematopoietic tissues" *Science* 276 (1997) 71-74. MSCs have been isolated and characterized from a variety of tissues including bone marrow, adipose tissue, and muscle. Zuk P A, Zhu M, Mizuno H, et al. "Multilineage cells from human adipose tissue: implications for cell-based therapies" *Tissue Eng.* 7 (2001) 211-228. It has been confirmed that MSCs derived from bone marrow and adipose tissue can be induced into non-mesenchymal neurogenic differentiation as well. Long X, et al. "Neural cell differentiation in vitro from adult human bone marrow mesenchymal stem cells" *Stem Cells Dev.* 14 (2005) 65-69.

HSCs also originate from the embryonic mesodermal germ layer and they are committed to form blood cell types including myeloid (monocytes and macrophages, neutrophils, erythrocytes, dendritic cells etc.), and lymphoid lineages (T-cells, B-cells, NK-cells). In addition to HSCs, several studies have demonstrated the hematopoietic differentiation potential of embryonic stem cells (ES) in vitro. See Moore K J, et al. "In vitro-differentiated embryonic stem cell macrophages: a model system for studying atherosclerosis-associated macrophage functions" *Arterioscler Thromb Vasc Biol.* 18 (1998) 1647-1654. It has been shown that ES derived macrophages display specific cell surface markers such as CD 14, CD4, CCR5, CXCR4, and HLA-DR. See Anderson J S, et al. "Derivation of normal macrophages from human embryonic stem (hES) cells for applications in HIV gene therapy" *Retrovirology* 3 (2006) 24.

Malignant transformation of hematopoietic cells is the common cause of diseases such as leukemia and myeloma. Treatment options for these malignant diseases are limited to chemotherapy, radiation therapy, and bone marrow or cord blood transplant. Each treatment strategy has its own limitations because none provide 100% elimination of transformed cells. Autologous bone marrow or stem cell transplants can be used to treat cancers in remission, however, frequent relapse of malignancies are reported following autologous transplantation of bone marrow since there is a relatively high chance that transformed cells persist in the bone marrow and are retransplanted from the bone marrow collection. Given that both MSCs and HSCs home to the bone marrow in post-embryonic life, it is believed that the bone marrow acts as a reservoir for occult transformed cells and that the malignant transformation is present already in stromal progenitors that escape the selection process typically applied to differentiate between malignant and non-malignant cells.

Due to the considerable risk that transformed or premalignant cells will be reintroduced via the autologous graft, methods of "purging" the graft population of transformed cells have been employed. These purging methods have included negative selection of CD34+ (a cell fraction enriched for HSC), negative selection of tumoral CD20+ cells, chemotherapy in vivo and other toxic treatments. Such procedures are expensive, difficult, not sufficiently effective, delay introduction of the graft, and may damage the cells to be engrafted. See Crippa F, et al. "Infectious complications after autologous CD34-selected peripheral blood stem cell transplantation" *Biol Blood Marrow Transplant* 8 (2002) 281-289. Subjecting the graft population to agents such as soluble FasL that are intended to selectively kill malignant cells has been suggested as an alternative. See US Patent Publication Serial No. 2008/0241109. Unfortunately, in each of these methods, complete elimination of malignant CD34+ cells is not possible. The cancer stem cell population in hematopoietic cancers such as leukemia is believed to be CD34+. See Bonnet, D. and Dick, J. E. "Human acute myeloid leukemia is organized as a hierarchy that originates from a primitive hematopoietic cell" *Nature Medicine* 3 (1997) 730.

Use of stem cells collected from the peripheral blood by apheresis also carries a possible or even likely risk of reintroduction of malignant cells because the collection procedure typically involves a mobilization of stem cells from the bone marrow by administration of growth factors such as GM-CSF and G-CSF prior to harvest. See e.g. Osiris U.S. Pat. No. 6,261,549 entitled "Human mesenchymal stem cells from peripheral blood." A typical process for autologous stem cell transplant includes four phases: an induction phase wherein conventional doses of chemotherapeutic agents are used to reduce the load of malignant cells; a mobilization/harvesting phase wherein growth factors are administered to the patient to induce the proliferation and mobilization of stem cells from the bone marrow into the bloodstream from which the cells are harvested by apheresis; a conditioning phase wherein total body irradiation or other high-potency treatment is administered to the patient to wipe out malignant cells and condition the patient to accept the transplant; and a final engraftment phase wherein stem cells are given back to the patient to reconstitute the immune system. Engraftment takes approximately two to four weeks to begin to be apparent enabling the patient to leave the confines of the hospital.

Recently, autologous HSC transplantation (HSCT) has been applied to the treatment of a large number of different autoimmune diseases including neurologic disorders such as multiple sclerosis, rheumatological disorders such as systemic sclerosis, rheumatoid arthritis, and systemic lupus, immunocytopenias such as immune thrombocytopenia, and inflammatory bowel disease, among others. In one large HSCT study for treatment of severe autoimmunity, stem cells were obtained from bone marrow in a minority of patients while in a majority, stem cells were obtained from the peripheral blood after mobilization with granulocyte colony-stimulating factor (G-CSF) or granulocyte-macrophage colony stimulating factor (GM-CSF). It is noted that mobilization has been associated with disease flares or lethal complications. Gratwohl A et al. "Autologous hematopoietic stem cell transplantation for autoimmune diseases" *Bone Marrow Transplantation* 35 (2005) 869-879.

Allogenic bone marrow stem cell transplantation is still the most commonly used procedure used to treat hematologic malignancies despite the likelihood of graft-versus-hostdisease (GVHD). In an allogeneic transplant, an HLA compatible donor's bone marrow cells are used to restore bone marrow after high dose chemo and radiation therapy. The disadvantage of an allogenic bone marrow stem cell transplant is the risk of GVHD, which affects the skin, liver and other organs and requires therapy with immunosuppressive drugs. While useful in the treatment of a number of other diseases, including aplastic anemia and other bone marrow failure states, amyloidosis, severe combined immunodeficiency and certain other inborn errors including thalassemia major, sickle cell disease and Wiskott-Aldrich syndrome, allogeneic transplants typically require ablative chemotherapy prior to transplantation.

What is needed is a source of cells that have the hematopoietic regenerative potential of bone marrows cells without the risk of contamination with occult transformed cells residing in the bone marrow compartment. Methods of generating such cells in sufficient in quantity and quality for clinical use have been problematic and there continues be an unmet need for this technology.

BRIEF SUMMARY OF THE INVENTION

The present invention is directed to methods for generation of cells dedicated to hematopoietic lineages for autologous cell therapy. The cells are derived from adipose tissue and induced to differentiate into the various hematopoietic lineages. The claimed invention is based on the novel recognition by the present inventors that tissue resident multipotent mesenchymal stem cells (MSCs) have the potential to differentiate to hematopoietic cells under selective conditions. In one embodiment, adipose tissue derived MSCs (ADSCs) adherent cells displaying a CD11b−, CD34−, CD45−, CD90+, and CD105+ phenotype were induced to become macrophages thus providing a source of such cells without resorting to collection of bone marrow. In other embodiments, adipose tissue derived MSCs (ADSCs) adherent cells are differentiated into one or more of neutrophils, eosinophils and dendritic cells. In certain embodiments, the adipose tissue derived MSCs (ADSCs) adherent cells are differentiated into a mixed hematopoietic lineage. In still further embodiments the ADSC are clonally isolated and induced to differentiate into desired lineages.

In still other embodiments hematopoietic progenitor cells are isolated and differentiated from mesenchymal stromal cells isolated from allogeneic or autologous adipose tissue. Adipose tissue is a preferred source of such cells because adipose tissue is an uncommon site for infiltration or occult residence of malignant cells. Therefore, only circulating but not tissue bound malignant cells are likely present in adipose tissue. The secure discrimination between malignant hematopoietic cells in the body and true MSC in the adipose tissue is based on the premise that tissue bound cells of the adipose tissue are considerably less likely to include any malignant cells. The present inventors have shown that hematopoeitic progenitor cells can be developed from CD45+/CD34− adherent mesenchymal cells isolated from adipose stromal tissue. This novel observation contrasts with the conventional wisdom that hematopoietic stem cells are of a separate lineage from mesenchymal cells and that hematopoietic stem cells are characterized by lack of adherent properties. In certain embodiments, adipose tissue is extensively washed to remove any cells that are not a part of the stromal vascular tissue. That is, removal of cells from the peripheral circulation that may include occult malignant or pre-malignant cells is accomplished.

In certain embodiments, any CD34+ cells in the SVF are removed by negative selection. Hematopoietic stem/progenitor cells are classically understood to have the CD34+ cell surface antigen (stem cells and colony-forming units). In normal peripheral blood, the number of CD34+ cells is about 0.1% of total mononuclear cells. Normal bone marrow typically contains about 1-2% CD34+ cells. Mobilization from the bone marrow increased the number of CD34+ cells to about 1-4% of total mononuclear cells. (In cord blood, CD34+ cells comprise about 0.1-1% of total mononuclear cells.) Thus, in this embodiment, in order to eliminate any possibility of contamination by malignant or premalignant cells of hematopoietic lineage, CD34+ cells in the SVF are removed by negative selection. If desired the remaining cells are then cultured in hematopoietic differentiation media.

In some embodiments, the adipose tissue derived cells are divided into adherent and non adherent subsets that are then subject to hematopoietic differentiating conditions. In one example for treatment of malignancies, autologous adipose tissue is removed from the patient and the nonadherent cells, which may be contaminated with occult cancer stem cells, are discarded. The adherent population is then subject to differentiation conditions that have been shown by the present inventors to result in hematopoietic differentiation. In other embodiments, both adherent and nonadherent cells are used as long the cells are derived from tissue extensively washed to reduce or remove peripheral blood contamination.

In certain embodiments, a population of hematopoietic stem cells for autologous transplant is generated by a method that includes cloning CD34 negative adherent adipose derived cells and selecting hematopoietic colony forming clones for transplantation. In one such embodiment, the adipose derived cells are cloned on a methylcellulose substrate. The adipose derived cells are cloned in one or more of: a selective cytokine milieu; a trainer cell extract; a trainer cell conditioned media; and a trainer cell co-culture. In some embodiments, the hematopoietic colony forming clones are determined to be free of cancer stem cells by performing single cell diagnostic PCR for known cancer causing genetic mutations on the clones and selecting those clones determined to be free of known cancer defects for expansion, hematopoietic In other embodiments where autologous cells are used for treatment of non-malignant conditions including autoimmunity, stromal vascular cells are isolated from autologous adipose tissue and are subject to hematopoietic differentiation without segregation into adherent and nonadherent populations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

For a more complete understanding of the present invention, including features and advantages, reference is now made to the detailed description of the invention along with the accompanying figures:

FIGS. 5A and B present the sequences of primers used in RT and real-time RT-PCR analyses.

FIG. 6A shows that upon stimulation with IL4 an increasing cell size of the differentiated ASCs was observed after an exposure time of 75 hours. FIGS. 6B and 6C show measurement of the cell sizes (based on 50 cells per culture) and reveal a lowering of numbers of cells below 30 microns in favor of an increase in the percentage of cells bigger than 30 microns. The number of cells over 30 microns increases significantly from 2% to 14% after stimulation with IL-4.

FIGS. 7A-C represent the results of a PCR based analysis of changes in gene expression before and after treatment with IL-4 and shows a characteristic up-regulation of HLA DR B1 and a decrease in CD4, CD8, CD68, and MCP-1 gene expression. LPS stimulation induces an increased expression of its receptor, CD14, and a diminished gene expression of CD4 via real-time PCR.

DETAILED DESCRIPTION OF THE INVENTION

Figure 1:
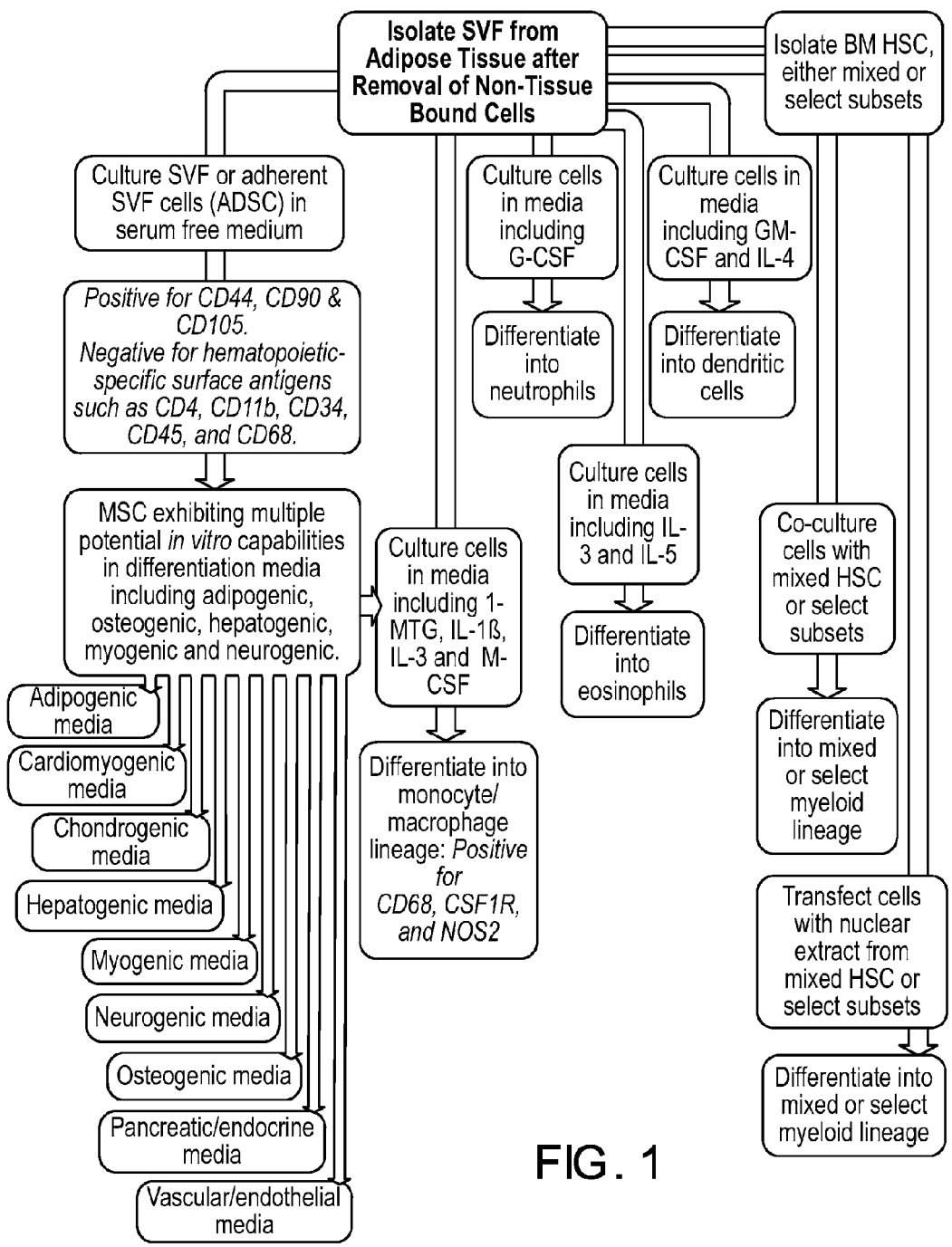
FIG. 1 provides a flow chart comparing generation of differentiated mesenchymal cells from MSC compared with generation of hematopoietic precursors in several embodiments.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

As described in further detail herein, the present inventors have determined that tissue resident multipotent mesenchymal stromal cells (MSCs) have the potential to differentiate to hematopoietic cells. The present inventors were able to identify, isolate and successfully separate tissue resident multipotent mesenchymal stromal cells (MSC) from adipose tissue and further derived methods of driving the differentiation of such adipose tissue resident multipotent MSC into differentiated hematopoietic cells, thus providing an expanded source of such cells for transplantation purposes free of malignant cells.

Proof of principal studies set out in Example 1 utilized clonally isolated adipose tissue derived adherent MSCs cells that displayed a cell surface CD11b−, CD34−, CD45−, CD90+, and CD105+ phenotype to evince the hematopoietic potential of such cells by eliminating the potential for derivation from contaminating hematopoietic stem cells from the peripheral blood. In one embodiment, such ADSC provide a new and readily available method of generating cells of the hematopoietic system that can be used for autologous transplant thus obviating the need for bone marrow transplant with its inherent risk of reintroducing occult malignant cells. Thus, in one treatment strategy disclosed herein, in which adipose tissue resident stem cells from patients with hematopoietic malignancy will be used to replace malignant hematopoietic cells in an autologous engraftment, the onset of relapse in autologous transplantation is avoided which in turn avoids the need for allogeneic transplantation with its risk of graft versus host disease.

ABBREVIATIONS: The following abbreviations are used throughout this application:
ADSC—adipose tissue-derived stromal cells
BM—bone marrow
ES—embryonic stem cells
HD—hematopoietic differentiated cells
HSC—hematopoietic stem cells
MSC—mesenchymal stromal cells
PLA—processed lipoaspirate
SVF—stromal vascular fraction To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Adipose tissue is highly vascularized and is thus a source of endothelial cells, smooth muscle cells, progenitor cells, and of early multipotent mesenchymal stromal cells. Adipose tissue is characterized by the presence of mature adipocytes bound in a connective tissue framework termed the "stroma." In the present invention, stromal cells generally refer to cells resident in the connective and vascular tissue of an organ or tissue. The stroma of adipose tissue includes an array of cells that do not include the lipid inclusions that characterize adipocytes. Non-limiting examples of such cells include fibroblasts, macrophages, monocytes, pericytes, endothelial cells, inflammatory cells such as monocyte/macrophages and lymphocytes, progenitors and early undifferentiated mesenchymal stem cells located in an intra- or peri-vascular location. Such cells also participate in tissue maintenance and repair, typically as supportive cells found to be located in an intravascular location.

Adipose derived stromal cells (ADSCs) are a population of tissue-resident multipotent mesenchymal cells that can differentiate into various lineages when grown in lineage-specific induction medium. ADSCs have certain characteristics similar to those of bone marrow-derived mesenchymal stromal cells (BM-MSCs). Compared with BM-MSCs, isolation of ADSCs is less invasive and yields a high yield per gram of tissue. The isolated ADSC have been shown to have adequate proliferative capacity and have thus been tested for use in tissue repair with promising results suggestive of application for repair of various tissue defects. See Katz, A. J., et al. Emerging approaches to the tissue engineering of fat. *Clin. Plast. Surg.* 26 (1999) 587-603, viii; Safford, K. M., et al. "Neurogenic differentiation of murine and human adipose-derived stromal cells" *Biochem. Biophys. Res. Commun.* 294 (2002) 371-379.

In 2005, the International Society for Cellular Therapy (ISCT) stated that the currently recommended term for plastic-adherent cells isolated from bone marrow and other tissues is multipotent mesenchymal stromal cells (MSC) in lieu of the prior "stem cell" term. MSC have been traditionally defined as spindle-shaped or fibroblast-like plastic adherent cells. Although originally isolated from bone marrow, MSC have now been isolated from a variety of tissues including bone periosteum, trabecular bone, adipose tissue, synovium, skeletal muscle, dental pulp and cord blood.

As used herein the term mesemchymal stem cell as is often used in the literature is instead referred to as Mesenchymal Stromal Cell (MSC) according to the definition adopted by the International Society for Cellular Therapy and published in a position paper by Dominici et al, *Cytotherapy* 8 (2006) 315. In accordance with the position paper, MSC must exhibit:
1) adherence to plastic in standard culture conditions using tissue culture flasks;
2) a specific surface antigen (Ag) phenotype as follows:
    positive ($\geq 95\%+$) for CD105 (endoglin, formerly identified by MoAb SH2), CD73(ecto 5' nucleotidase, formerly identified by binding of MoAbs SH3 and SH4), CD90 (Thy-1), and
    negative ($\leq 2\%+$) for CD14 or CH11b (monocyte and macrophage marker), CD34 (primitive hematopoietic progenitor and endothelial cell marker), CD45 (panleukocyte marker), CD79α or CD19 (B cells), and HLA-DR (unless stimulated with IFN-γ); and
3) tri-lineage mesenchymal differentiation capacity: able to differentiate in vitro into osteoblasts, adipocytes and chondrocytes in inductive media.

MSCs have been traditionally defined as spindle-shaped or fibroblast-like plastic adherent cells. Although originally isolated from bone marrow, MSC have now been isolated from a variety of tissues including bone periosteum, trabecular bone, adipose tissue, synovium, skeletal muscle, dental pulp and cord blood. It has been shown that MSCs derived from bone marrow and adipose tissue can differentiate into non-mesenchymal lineages as well, by induction of their respective differentiation potential.

When the connective tissue of adipose tissue is enzymatically digested (with for example collagenase), the lipid containing adipocytes can be separated from the other cell types. In 1964, Rodbell reported the use of collagenase to dissociate adipose tissue into a cellular suspension that could then be fractionated by centrifugation into an upper, lipid-filled adipocyte fraction, and a cell pellet comprised of non lipid-filled cells. The pelleted non-adipocyte fraction of cells isolated from adipose tissue by enzyme digestion has been termed the "stromal vascular cell" or "SVF" population. (Rodbell M. "Metabolism of isolated fat cells: Effects of hormones on glucose metabolism and lipolysis" *J. Biol. Chem.* 239 (1964) 375-380).

Heretofore, adipocytes have been separated from the SVF by centrifugation wherein the adipocytes float and the cells of the SVF pellet. Typically however, the SVF is subject to further processing and selection, including plastic adherence. Cells from the stromal vascular fraction that have been subject to plastic adherence are typically referred to as cultured stromal vascular cells or "adipose tissue-derived stromal cells" (ADSC). Notwithstanding other definitions that may exist in the art, as used herein, the term "stromal vascular fraction" or "SVF" cells refers to all of the constituent cells of adipose tissue after enzyme digestion and removal of adipocytes and are not limited to plastic adherent cells.

Transplantation of cells from murine adipose stromal vascular fractions has been shown to rescue lethally irradiated mice when transferred at the same time or shortly after irradiation. Cousin B, et al. "Reconstitution of lethally irradiated mice by cells isolated from adipose tissue" *Biochem Biophys Res Commun.* 301 (2003) 1016-1022. However, it is stated by the authors that this was due to the ability of the adipose stromal vascular cells to support survival of injured cells in the bone marrow which were then able to recover and regenerate rather than a consequence of new generation of HSC derived from the adipose cells themselves as is the focus of the present invention. Since ADSCs have been shown to secrete anti-apoptotic cytokines such as IGF and VEGF, which are able to enhance the survival of cells that would otherwise die, in certain embodiments, before and at the time of transplantation of the ADCD or the modified ADSCs, tissue resident bone marrow cells that are potentially malignant are destroyed by radiation, chemotherapy, or a combination thereof, including by prior mobilization. Mobilization may be induced not only by GCSF, but also by inhibiting CXCR4 dependent binding. This eradication protocol aims to prevent newly transplanted ADSC from rescuing residual malignant cells in the bone marrow.

Recently, hemangioblasts have been identified in a CD45– KDR+ CD105+ subset of nonadherent SVF from human adipose tissue. Minana M D, et al. "IFATS collection: Identification of hemangioblasts in the adult human adipose tissue" *Stem Cells* 26 (2008) 2696-2704. It has also been reported that adipose tissue derived stem cells express angiogenic and hematopoietic factors. Kilroy G E, et al. "Cytokine profile of human adipose-derived stem cells: expression of angiogenic, hematopoietic, and pro-inflammatory factors" *J Cell Physiol.* 212 (2007) 702-709.

Several studies have suggested that phenotypically normal and functionally competent cells of hematopoietic system could be derived from ES cells, bone marrow HSCs, or peripheral blood HSCs. See Karlsson K R, et al. "Homogeneous monocytes and macrophages from human embryonic stem cells following co-culture-free differentiation in M-CSF and IL-3" *Exp Hematol.* 36 (2008) 1167-1175. ES derived macrophages display characteristic cell surface markers CD 14, CD4, CCR5, CXCR4, and HLA-DR. Anderson J S, et al. "Derivation of normal macrophages from human embryonic stem (hES) cells for applications in HIV gene therapy" *Retrovirology* 3 (2006) 24.

Neutrophils have been generated from murine ES (Lieber J G, et al. "The in vitro production and characterization of neutrophils from embryonic stem cells" *Blood* 103 (2004) 852-859) and human peripheral blood CD34+ hematopoietic stem cells (Hino M, et al. "Ex vivo expansion of mature human neutrophils with normal functions from purified peripheral blood CD34+ haematopoietic progenitor cells" *Br J Haematol* 109 (2000) 314-321).

Unfortunately, isolation of cells from bone marrow is a painful and potentially dangerous procedure and, in the treatment of malignancies, further suffers from the risk that occult malignant and pre-malignant cells may be maintained in the bone marrow despite selection fractionation prior to re-transplant. Use of peripheral blood stem cells is complicated by the rare nature of these cells and that they must be collected by apheresis after treatment to induce mobilization of cells from the bone marrow. However, such treatment not only mobilizes malignant and pre-malignant cells but is associated with other adverse effects.

The present inventors have developed methods of specific isolation of MSCs from readily available adipose tissue that eliminates the risk of malignant cell contamination and have driven the differentiation of these cells to a hematopoietic linage for reconstitution. Thus mechanisms of in vitro differentiation of adipose tissue derived MSCs present have been determined and identified and conditions have been established for directed differentiation of ASCs toward a particular hematopoietic lineage. In one embodiment, a method for efficient generation of cells with hematopoietic characteristics from MSCs through expansion of clonally isolated multipotent mesenchymal cells is provided. The functionality of the generated cells and attributes that are characteristic for cells of the macrophage/monocyte lineage are disclosed.

As provided herein, isolating and culturing adherent MSCs in differentiation media containing cytokines resulted in generation of morphologically normal cells with distinct hematopoietic characteristics. As set out in Example 1 herein, a proof of principal experiment was conducted to determine derivation of hematopoietic cells from ADSC. A primary ADSC population was isolated from a cohesive piece of abdominal adipose tissue in order to lower any potential of contamination with hematopoietic cells which, given the traumatic nature of harvest, will typically be found within lipoaspirate samples. The ADSC clones used in the proof of principal study displayed mesenchymal characteristics such as a CD44+, CD90+, CD105+, CD45−, CD34−, CD4−, CD11b−, CD14− and CD68− phenotype, indicating the absolute absence of any hematopoietic progenitor cells. To exclude any contamination possibility, the clones were examined for hematopoietic specific surface markers (CD34, CD45, CD68, CD11b) for 5 consequent passages. In addition, adipogenic, osteogenic, hepatogenic, chondrogenic and neurogenic studies confirmed the multilineage potential of ADSC clones.

Incubation of ADSC clones in a cocktail of cytokines resulted in a significant alteration in cell morphology from spindle to round shaped cells. Simultaneously, as the differentiation proceeded, cells lost adherence capabilities. The components of the differentiation media, such as IL-1β, IL-3 and macrophage-colony-stimulating factor (M-CSF), were selected from the panoply of available cytokines and growth factors based in part on the inventor's appreciation of the role of these factors in macrophage development. Of these, IL-3 and M-CSF have been used to induce macrophage differentiation in vitro from ES. See e.g. Karlsson K R, et al. "Homogeneous monocytes and macrophages from human embryonic stem cells following co-culture-free differentiation in M-CSF and IL-3" *Exp Hematol* 36 (2008) 1167-1175. The present inventors determined that functional hematopoietic cells could be developed from cells isolated from adipose tissue thus providing an important new source of stem cells for autologous transplantation.

ADSC driven towards hematopoietic development under the chosen culture conditions were shown by transcriptomic analysis to express c-KIT and PROM-1, which indicates a genomic shift toward the hematopoietic lineage. Expression of these genes together with CD4 and CD8 are known to be associated with hematopoiesis of HSCs in bone marrow. See Ratajczak M Z, et al. "The c-kit proto-oncogene in normal and malignant human hematopoiesis" *Int J Cell Cloning* 10 (1992) 205-214. Additionally, the pronounced expression of the chemokine receptor CCR5, IFNGR1, CD14, MCP1, HLA-DR B1, and to a lower extent CD32 and CD64, evinces the tendency of these cells to differentiate into immunocompetent cells such as granulocytes, T-cells or monocytes/macrophages.

Moreover, hematopoietic differentiated (HD) cells developed as disclosed herein possess the necessary elements to recognize pathogen associated structures, such as LPS via CD14 and to opsonize IgG Fc fragments (via CD32, CD64). Expression of HLA-DR refers to the antigen presenting cell (APC) characteristic of macrophages. Most significantly, the expression of CD68 and CD11b as specific monocyte/macrophage markers, substantiated by MRC1, CSF1R, IL-10, TNF up-regulation, distinguishes the differentiated ADSCs as macrophage-like cells. Immunocytochemistry data confirmed the presence of CD68, CSF1R and the macrophage specific NOS2 protein. CSF1R mediates several functions of cytokine CSF-1 and has been shown to selectively promote macrophage maturation during differentiation of HSCs. See Heusohn F, et al. "Coordinate expression of the lineage-specific growth factor colony-stimulating factor (CSF)-1 and its receptor selectively promotes macrophage maturation during differentiation of multipotential progenitor cells" *Cell Growth Differ.* 5 (1994) 1119-1126.

NOS2 encodes the nitric oxide (NO) synthase, which is induced by LPS. It is known that some cytokines produce NO as part of the oxidative burst of macrophages. Moreover the enzyme activity of α-naphthyl acetate esterase, as a member of cellular carboxyl esterases, is a marker of monocytes/macrophages that could be very well detected in the HD cells. See Soufleris A J, et al. "Cytologic characterization of pulmonary alveolar macrophages by enzyme histochemistry in plastic" *J Histochem Cytochem.* 31 (1983) 1412-1418. Although the exact role of α-NSE has not been completely described, it is known to be associated with inflammatory processes and may play a role in the pathogenesis of chronic inflammatory diseases. Kolios G, et al. "Depletion of non specific esterase activity in the colonic mucosa of patients with ulcerative colitis" *Eur J Clin Invest.* 32 (2002) 265-273. The detected expression of CD68 and CD11b, together with CD14 and MRC1, suggests the ability of HD cells to ingest particles, since these genes are highly involved in mediating the process of phagocytosis in hematopoietic derived macrophages. This finding signifies that the macrophage-like cells derived from ASCs share one of the key functions with naturally occurring macrophages.

Further functional analyses indicate that HD cells, similar to macrophages, respond to IL-4 and LPS stimulation. LPS, as a component of bacterial membrane, and is known to be a potent activator of immunocytes, effective via CD14, TLR-2, TLR-4 and LY-86 (MD-2) receptors. LPS initiates the classical activation of macrophages and leads to the release of pro-inflammatory cytokines such as IL-1, IL-6, TNFα, MCP1, and IL-10. Similarly, as seen in macrophages, HD response to LPS stimulation was evidenced by a strong up-regulation of CD14. The expression of CD4 in LPS stimulated HD cells decreased simultaneously and this phenomenon has previously been reported in primary human macrophages. Data obtained from stimulation experiments also indicate an increase in the concentration of IL-2, IL-10 and IL-17 after stimulation with LPS.

IL-4 activates the alternative pathway which is associated with a predominantly anti-inflammatory microenvironment (e.g. release of IL-5, IL-13, TGFβ but a down-regulation of IL-1, IL-6, IL-8 and TNFα). IL-4 stimulation of HD resulted in up-regulation of HLA DRB1 expression. The increase of major histocompatibility complex class II in stimulated HD cells, an important factor in presenting extracellular antigens, is similar to the capacity of macrophages as APCs. Moreover, it has been known that IL-4 promotes differentiation of monocytes to dendritic cells, a potent APC. In this context an increasing cell size has been described upon stimulation with IL-4 which corroborates the same phenomenon observed by certain of the present inventors in IL-4 stimulated HD cell. IL-4 stimulation further diminished CD68, CD4 and CD8, and MCP-1 expression which is congruent with findings on human monocytes. Moreover, the enhanced release of IL-5 and IL-13 and the decreasing concentration of IL-2 after IL-4 stimulation support this data.

It has been shown that undifferentiated ADSCs can also be stimulated with LPS and IL-4. Kilroy G E, et al. Cytokine profile of human adipose-derived stem cells: expression of angiogenic, hematopoietic, and pro-inflammatory factors. *J Cell Physiol.* 212 (2007) 702-709. However, in the experiment presented here this ADSCs response was lower and/or could be found at a later time point. IL-1α was exclusively released in the differentiated cells upon LPS stimulation and furthermore decreased upon exposure to IL-4. Interestingly, following IL-4 stimulation, IL-13 and the low secreted cytokines (TNFα, TNFβ, IFNγ) were detected in higher concentrations in undifferentiated ADSCs than the HD cells. The fact that macrophages are extremely heterogeneous and their reaction to various stimuli or microenvironments are diverse (Gordon S, Taylor P R. "Monocyte and macrophage heterogeneity" *Nat Rev Immunol.* 5 (2005) 953-964), makes it difficult to rate the actual maturation level of macrophage-like HD cells. However, the data suggests that the macrophage-like HD cells respond to stimuli via either classical or the alternative pathways.

The ability to obtain phenotypically normal and functionally competent cells of hematopoietic system from multipotent mesenchymal cell isolated from readily available tissue, especially adipose tissue, provides a particularly useful addition to the resources available for autologous cell transplants, particularly in the treatment of malignancies wherein the BM compartment may be compromised by the presence of occult malignant cells.

EXAMPLE 1

Cell Culture

Human adipose tissue specimens were obtained from healthy donors (n=43; age 17-33, mean=27.6) under Institutional Review Board (IRB) approved protocols. ADSCs were isolated from gross specimens as described in Izadpanah R, et al. "Biologic properties of mesenchymal stem cells derived from bone marrow and adipose tissue" *J Cell Biochem.* 99 (2006) 1285-1297. Approximately 50 g of adipose tissue was cleaned extensively by washing to remove any non-tissue adherent contaminating cells followed by mincing and digesting the tissue with Collagenase Type I (Gibco, InVitrogen, Carlsbad, Calif.) for 60 min at 37° C. After treatment with an RBC lysis buffer (BioWhittaker, Walkersville, Md.), cells were counted and plated at a fixed density in alpha-MEM medium, supplemented with 20% fetal bovine serum (Atlanta Biological, Atlanta, Ga.), 1% L-Glutamine (Cellgro, Herndon, Va.) and 1% Penicillin/Streptomycin (Cellgro) at 37° C. with a 5% $CO_2$ atmosphere. Cells were passaged upon reaching 70% confluence. Clones were generated by plating the cells in serum free medium at a concentration of a single cell per well on ultra low-adhesion 96 well plates. The culture dishes were inspected on day 1 to confirm the presence of one cell per well. A total of 19 clones were available within 7 days. Seven out of 19 clones failed to grow in serum free medium, and the remaining 12 viable clones were continuously cultured to confluency, and expanded for further characterization.

Immunocytochemistry ("ICC"): ADSC and differentiated cells were cultured on sterile chamber slides and fixed by incubation in 1% paraformaldehyde (PFA)/PBS for 3-5 min, permeabilized with 0.5% Triton X-100 in PBS for 15 min, and postfixed for 10 additional minutes in 4% PFA in PBS. As a positive control, histology slides were coated with buffy coat from CD34+ enriched peripheral blood samples by cytospin (400 rpm for 8 min), fixed with 1% PFA in PBS and stored in −80° C. until ICC was accomplished. The fixed slides were incubated with human specific primary antibodies for 3 h at a final concentration of 0.02-0.04 mg/ml, and after a washing step with PBS, 0.002 mg/ml of the matching secondary antibody was added. The signal was detected with a Leica TCS SP-2 confocal microscope equipped with one Argon (457-477 nm; 488 nm, 514 nm) and two HeNe lasers (543 nm; 633 nm) at a magnification of HCX PL APO 63×/1.4 at 21° C. Data was processed with Leica confocal software. Immunocytochemistry analyses of cells cultured to drive toward a hematopoietic lineage revealed the expression of hematopoietic lineage specific antigens CD68, CSF1R, and NOS2. All these antigens were readily detectable in HD and BM cells; however, undifferentiated ASCs were negative for them (data not shown).

Figure 2:
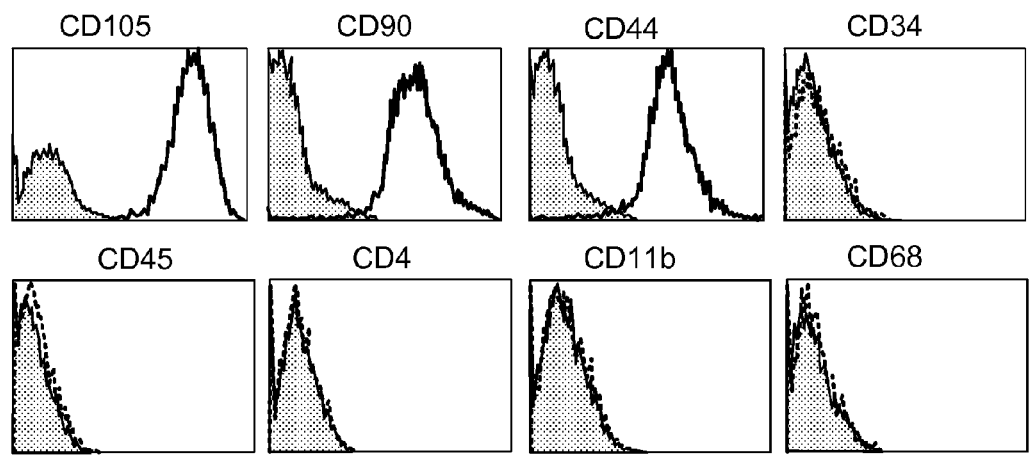
FIG. 2 represents characteristics of human adipose tissue derived mesenchymal stem cells by FACs analyses of ASC clones at passage 4. Black line, control IgG; dashed line corresponding antibody. Data are representative of three independent clonal ASCs.

Immunophenotyping of single cell clones by flow cytometry (FACS) of trypsin-dissociated ASCs cultures was performed on a Beckman-Coulter Epics FC500 flow cytometer. The analysis revealed that the adherent clones express the mesenchymal markers such as CD90, CD105, CD44, but these do not express the hematopoietic-specific surface antigens such as CD45, CD4, CD11b, CD34, and CD68 (Histographs representative of triplicate experiments are depicted in FIG. 2). All clones demonstrated equivalent colony formation potential.

Multilineage Potential: The multilineage potential of ADSCs was examined by performing adipogenic, osteogenic, hepatogenic and neurogenic differentiation as previously described in Izadpanah R, et al. "Characterization of multipotent mesenchymal stem cells from the bone marrow of rhesus macaques" *Stem Cells Dev.* 14 (2005) 440-451. ASCs were isolated from human adipose tissue by collagenase digestion of the tissue, differential centrifugation, and expansion in culture. In an analysis of specimens obtained from 42 individual donors, a mean of 247,401±136,514

ASCs from a single milliliter of liposuction effluent was recovered within a 6.0±2.4 day expansion period. After passage in vitro, these cells, which are identified herein as Adipose-derived Stem or Stromal Cells (ADSC), exhibit a differentiation potential comparable to that of bone marrow derived Mesenchymal Stem Cells (BMSCs). Within 2-3 passages after the initial plating of the primary culture, ADSCs appear as a monolayer of broad, flat cells having a diameter of 20-30 µm. BMSCs showed heterogeneous groups of low contrast flat cells together with smaller, more spindle-shaped cells. Single cell ASC and BMSC cultures generated CFU (colony forming unit) clones after 2 weeks of culture, indicating the potential for self-renewal.

BMSCs and ADSCs did not spontaneously differentiate during in vitro culture expansion. Using lineage specific differentiation culture media, MSCs displayed the capability of generating adipocytes as detected by staining with an Oil Red-O solution (Diagnostic Biosystems). Osteogenic lineage capacity was detected by an increase in calcium deposition as identified by Alzarin Red (Fluka), and chondrogenesis was confirmed by Toluidine Blue staining of extracellular proteoglycans. Hepatogenesis and neurogenesis differentiation was verified by albumin and MAP2 staining respectively. All clones had equivalent colony formation potential; furthermore, these lines displayed multiple in vitro differentiation capabilities. Chondrogenic induction of ADSCs and BMSCs, under micromass conditions, resulted in cell condensation and nodule formation by 3-4 weeks. Nodules at this time point stained positive for Safranin O.

For analysis of clonally derived populations of ADSCs, low density cell culture (50-100 cells/10 cm dish) was performed. ASCs underwent an average of three population doublings prior to the first passage. It was determined that an average of 95% of the CFU derived from single cell can differentiate into mesodermal lineages (adipogenic, osteogenic, and chondrogenic) after 20 days in lineage specific induction media.

Induction of Neural Cell Lineage Protein Expression in MSCs: ADSCs and BMSCs were induced along a neural lineage through neurosphere formation. The final stage of neurodifferentiation was completed on PDL-laminin coated substrate for 10-15 days in Neurobasal (NB) media (Invitrogen), supplemented with B27, bFGF, and EGF. Differentiated cells were analyzed via the detection of neuronal markers (MAP-2, NeuN, and NF160) and the astrocyte marker, GFAP. During neural induction in NB media, both cell populations undergo a marked morphologic change from elongated fibroblast morphology to compact, spheroid bodies which expand to larger spheroid bodies as the total cell number expands. Neural induction was performed after detachment of the spheroid bodies from the substrate. Intact or dissociated NS were layered on the PDL-laminin coated chamber slide and cultured for an additional 10 days. As soon as the cells were layered on the laminin-coated surface, spheroid cell masses began to adhere and spread across the growth surface and began forming long chains of cellular processes. Finally, the cell processes began to exhibit secondary branching with multiple extensions. To additionally characterize the ASC-derived neurospheres, both immunocytochemistry and Western blot analyses were performed for specific antigens indicative of neural cell lineages. The data from these experiments indicate that ADSC derived neurospheres express high levels of Nestin, MAP-2, GFAP, and CD133 (data not shown). ASC-NS cells were subsequently differentiated on laminin coated surfaces for 10 days. The increase in neural lineage related protein expression upon neural induction was confirmed using RT-PCR analysis (data not shown) and immunostaining for MAP2, NeuN, NF160, astrocyte marker, GFAP, and Nestin. Intense MAP2 expression and strong nuclear staining for NeuN in ADSCs was observed following neurosphere differentiation. High levels of GFAP, which is absent in undifferentiated ADSCs, were present after neurosphere differentiation. Prominent Nestin expression in ADSC-derived neurospheres was also observed.

Hematopoietic Differentiation: Cells were plated at a density of 5000 cells per $cm^2$ on plastic in either a cell culture dish (Greiner Bio-One) or chamber slides (Nulge Nunc International) and grown at 37° C. and 5% $CO_2$. Cells were cultured in formulated differentiation media consisting of α-MEM, 10% FBS, 0.1 µl/ml 1-monothioglycerol ("MTG", Sigma-Aldrich), supplemented with 100 U/ml IL-1β (Sigma), 500 U/ml IL-3 (Prospec Bio), and 20 U/ml M-CSF (Prospec Bio) as stimulating substances. Thirty percent (30%) of the primary volume was augmented with fresh media every 2 days for 12 days. ADSC clones cultured in differentiation media (supplemented with cytokines+0.1 µl/ml MTG) displayed characteristic altered morphology within 9 days towards a round shape associated with a decreasing adherence. LM-micrograph analysis of the ASC culture during undergoing differentiation demonstrated similarities in shape and outer appearance with that of human monocytes/macrophages. Cells cultured in control media (α-MEM+10% FBS+0.1 µl/ml MTG) revealed no change in morphology or adherence after 3 days and 9 days.

After about 12-15 days of differentiation, cells started losing their adherence to the cell culture dish. The morphology of hematopoietic differentiated (HD) cells derived from all ASC clones appeared similar. These results were found to be consistent in replicated experiments. Cell growth and proliferation ceased upon the initiation of morphological change into HD cells. Control cultures showed no morphologic alteration. Cell cycle analysis of HD cells showed cell cycle arrest at the S-phase indicating an arrest of cell proliferation. However, the entire population remained diploid after 12 days of differentiation (data not shown).

Reverse Transcription-PCR: Hematopoietic lineage specific gene expression was assessed on HD cells compared with bone marrow (BM) cell controls. Several genes were selected to analyze the process of differentiation and level of maturation of HD cells, ranging from hematopoietic markers (c-KIT, PROM1, CD4, CD8) to non-specific macrophage/monocyte markers (IFNGR1, CD32, CCR5, HLA-DRB1, TNF, IL10, CD14) and specific macrophage/monocyte markers such as CD68, CD11b, MRC1, CSF1R and CCL2.

Total cellular RNA was isolated from cultures using an RNeasy mini kit (Qiagen, Valencia, Calif.). The High Capacity Reverse Transcription Kit (Applied Biosystems, Foster City, Calif.) was used to obtain cDNA. Thermocycling was performed at 95° C. for 3 min, followed by 34 cycles at 94° C. for 45 sec, Tm for 45 sec, 72° C. for 60 sec completed by additional 10 min 72° C. and ∞ at 4° C. according to the primer sequences set out in FIGS. 5A and 5B.

Figure 3:
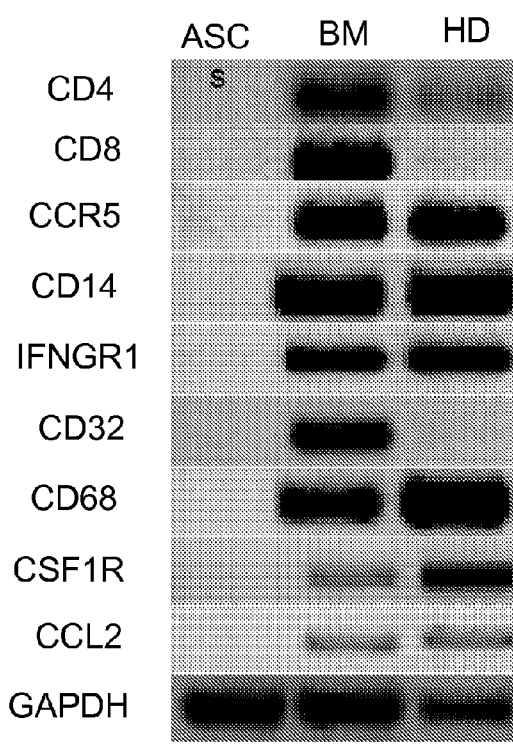
FIG. 3 depicts the results of hematopoietic specific gene expression by RT-PCR in undifferentiated ADSCs (ADSCs), positive control (BM) and hematopoietic differentiated ADSCs (HD).

Gene expression analysis using semi-quantitative RT-PCR as shown in FIG. 3 revealed that, upon the onset of differentiation, CD4 was rapidly up-regulated in hematopoietic HD after 9 days of differentiation, however CD8 expression in HD was only slightly higher than undifferentiated ASCs. Hematopoietic progenitor cells obtained from bone marrow (BM) served as positive control in these experiments. Analyses of nonspecific macrophage/monocyte markers revealed a significant up-regulation of CD14 in HD cells comparable to the expression of this gene in BM cells.

CCR5 expression was also slightly higher in HD cells than in control BM cells. A small reduction of interferon γ receptor (IFNGR1) expression was observed in HD cells compared to BM cells (78%). There was a weak expression of CD32 (Fc fragment of IgG, low affinity IIb) in HD cells (~10% of the positive control). Significant up-regulation of markers of specific and mature macrophages was observed in HD cells, most significantly, CD68 was seen to be strongly expressed. About a two-fold increase in the Colony stimulating factor 1 receptor (CSF1R) expression was seen in HD cells as compared to BM cells. Additionally, monocyte chemoattractant protein-1 (a.k.a. CCL2) expression was similar in HD and BM cells. The expression of this gene was undetectable in undifferentiated ASCs (FIG. 3).

Real-time Reverse Transcription-PCR was performed using SYBR Green Master Mix (Invitrogen) in a 2 step protocol (50 cycles of 10 sec at 95° C. and 45 sec at Tm). The data was generated with an iCycler My iQ from Biorad with iQ5 V2.0 software for analysis. As equation for fold changes 2-ΔΔCT has been used, based on the ΔΔCT method. For non detectable genes a threshold cycle of 40 was chosen, thus CT values of 40 and above was considered as not expressed.

Figure 4A:
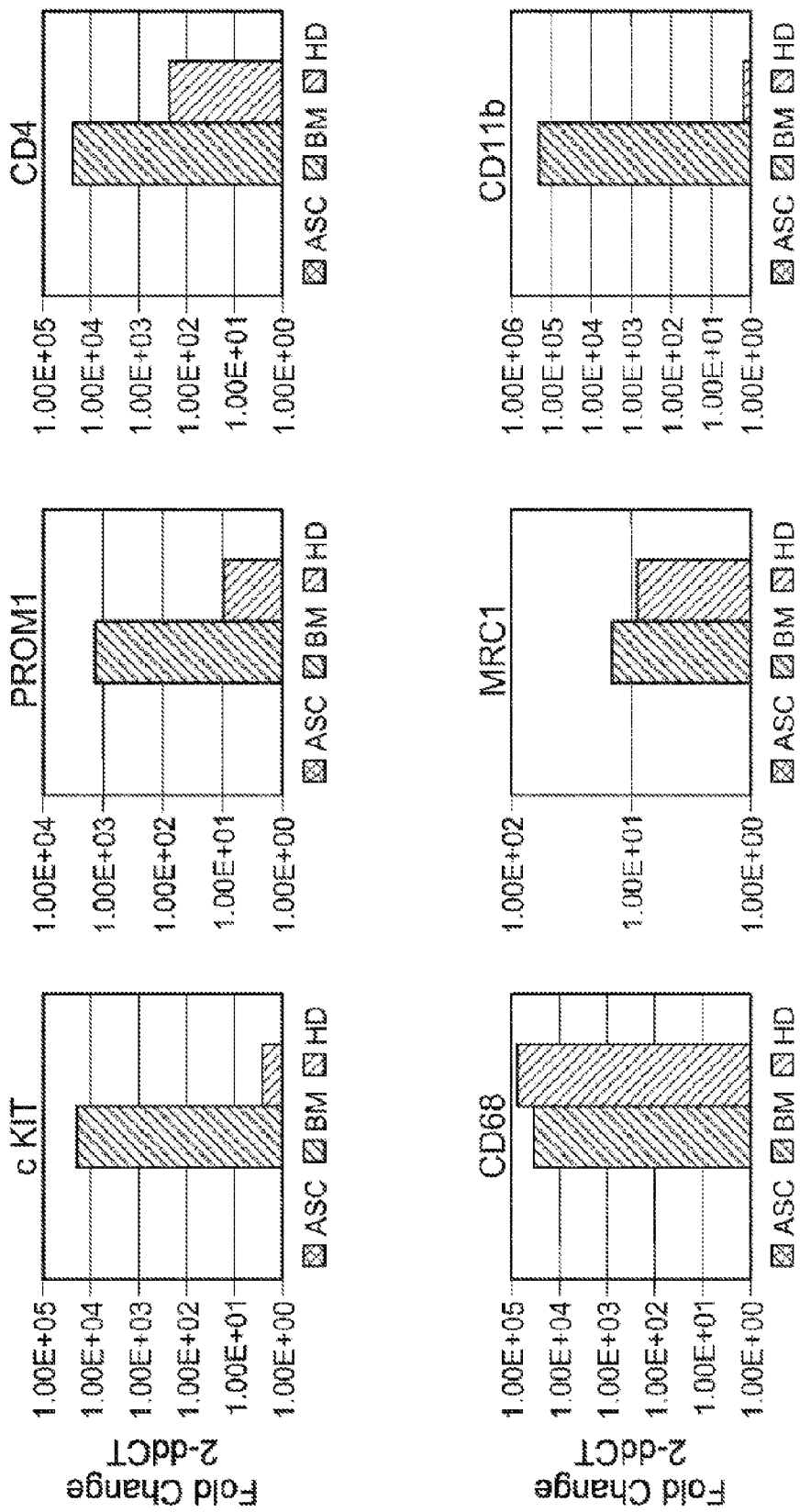
FIGS. 4A and B show the results of analysis of hematopoietic gene expression by real-time PCR comparing ADSC, BM and hematopoietic differentiated ADSCs (HD).
Figure 4B:
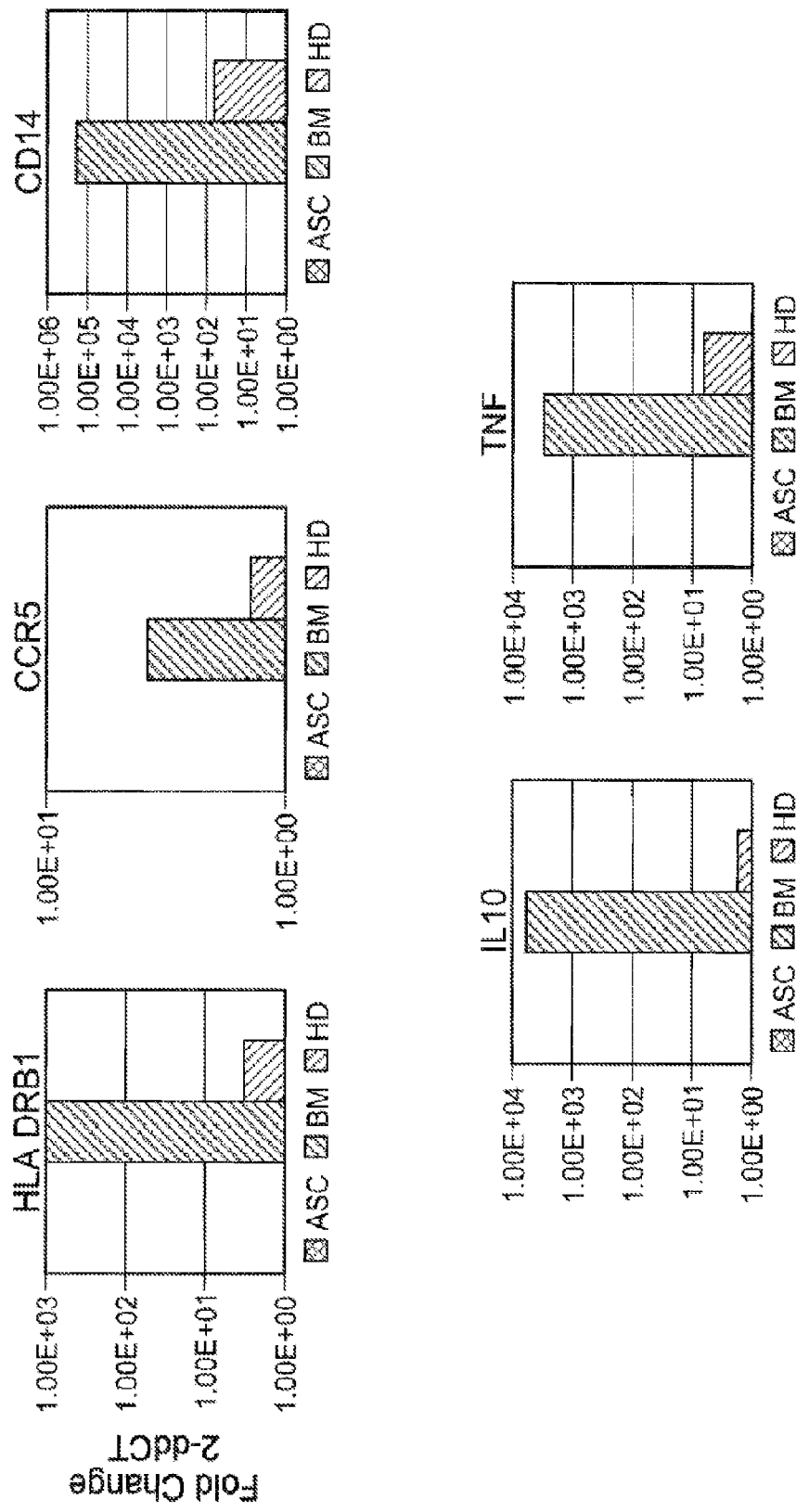

The quantitative real-time PCR analysis results on FIGS. 4A and 4B showed a significant increase in the expression of the hematopoietic progenitor genes CD4, PROM1, and c-KIT (484.4, 79.4, and 20.45 fold, respectively). mRNA coding for IL-1beta and IL-3 receptor genes have been detected in HD cells (2.4±0.6 and 1.8±0.3 respectively; n=3). IL-1beta has a role in regulation of transcription factors such as nuclear factor kappa B. HD cells exhibit an elevation in nuclear factor kappa B expression (2.7±0.4; n=3, P<0.05). Compared to undifferentiated ASCs, weak expression of GATA and PU.I genes (1.08±0.1 for GATA and 1.9±0.3 for PU.1; n=3) was observed in HD cells. There was a significant up-regulation of some of the non-specific monocyte/macrophage markers such as CD14 (100 fold), major histocompatibility complex class II (HLA DRB1) (13.6 fold), TNF (53 fold), CCR5 (43 fold), and IL10 (7.2 fold) in HD cells. Among the monocyte/macrophage specific genes, strong expression of CD68 was observed in differentiated ADSCs (~240% of BM cells). In addition, the expression of integrin α encoding CD11b (500 fold) and mannose receptor 1 (MRC1) (72 fold) was increased.

The potential of ADSCs to give rise to cells from hematopoietic lineage was evidenced by the expression of lineage specific antigens CD68, CSF1R, and NOS2, as shown by immunostaining, while undifferentiated ADSCs were negative for these antigens.

Among unspecific markers of monocyte/macrophage lineage, CCR5 was found to exhibit higher expression in the differentiated ADSCs than in the bone marrow control, as detected by real-time PCR (rtPCR). Additionally, the major histocompatibility complex class II (HLA DRB1), which exists specifically on antigen presenting cells, and the cytokines TNF and IL10 were expressed upon exposure to the formulated differentiation media. CD14, which encodes the lipopolysaccharide receptor, was abundantly expressed on the differentiated cells. Most importantly, the macrophage specific markers CD68 and CD11b were expressed as well as MRC1 (2 fold). Undifferentiated ASCs did not show expression of any of the aforementioned mentioned genes. GAPDH served as housekeeping gene and was expressed in all samples.

Functional Assays: The aforementioned data showed that HD cells express characteristics similar to that of macrophages. However, an important function of the macrophage is its ability to phagocytose foreign material. The phagocytic capability of HD cells was evaluated using fluorescent-labeled E. coli particles. Functional differentiation of cells was determined by incubating the cells with Alexa Fluor labeled E. coli beads (Molecular Probes) at a final concentration of 100 particles per cell for 2 hours. Cells were washed twice with PBS and imaged using a Leica TCS SP-2 confocal microscope. Unlike the undifferentiated ASCs, more than 95% of HD cells that showed macrophage-like morphology were capable of actively phagocytosing the E. coli particles (data not shown). The undifferentiated ASCs however did not show any phagocytic activity.

In addition, HD cells exhibit enzymatic activity of α-naphthyl acetate esterase (nonspecific esterase) exclusively, which is a property of macrophages. See Stadnyk A W, et al. "Characterization of nonspecific esterase activity in macrophages and intestinal epithelium of the rat" J Histochem Cytochem. 38 (1990) 1-6. Non specific esterase activity was determined by using the α-Naphthyl Acetate Esterase Kit (Sigma-Aldrich) according to manufacturer's instructions. According to the methodology, α-naphthyl acetate is enzymatically hydrolyzed, liberating a free naphthol which couples with a diazonium compound, forming black colored deposits at the sites of non-specific esterase enrichment. The result was interpreted based on bone marrow cell staining (positive control) or undifferentiated ASCs (negative control). About 36.26% of HD cells were found enzymatically active (0.3626±0.0734; n=10).

Figure 6A:
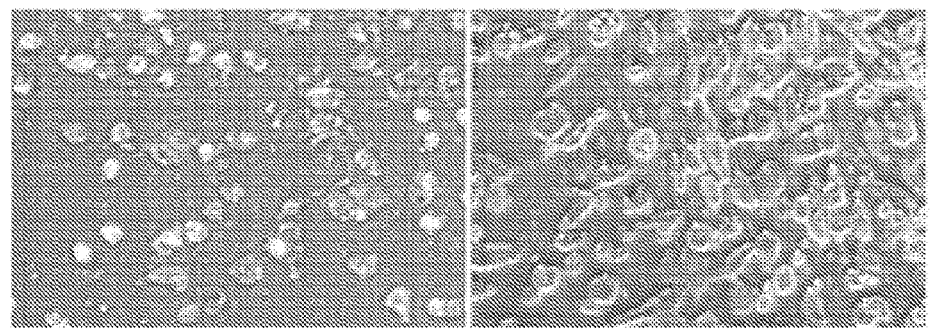
FIGS. 6A-C show the results of IL-4 and LPS stimulation of differentiated ASCs.
Figure 6B:
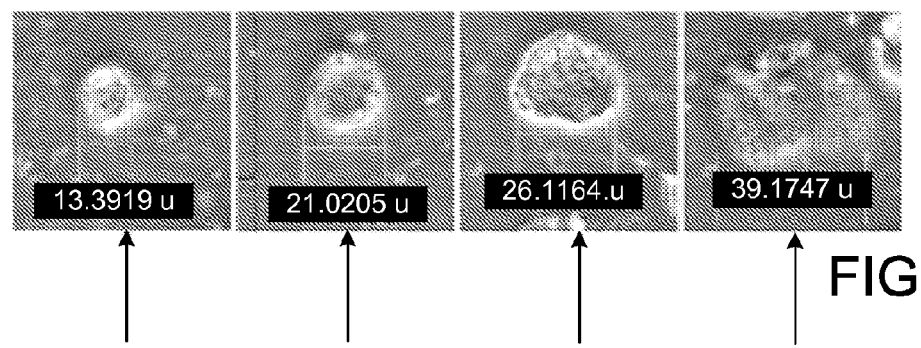
Figure 6C:
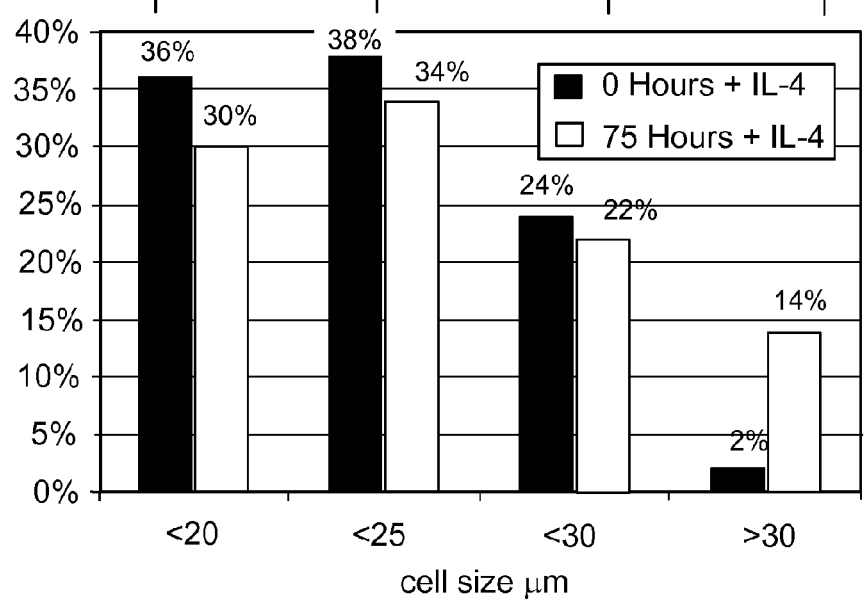

Macrophages, as effector cells, play a key role in the inflammatory response and release various cytokines in response to major stimulators, such as IL4 and LPS. To elucidate if HD cells exhibited such phenomenon, the differentiated cells as well as the control cultures were activated with 20 ng/ml IL-4 (PeproTech Inc.) for 5 days or with 1 μg/ml lipopolysaccharide (LPS) from E. coli 0127:B8 (Sigma) for 3 days. Additionally, supernatants from the cultures were harvested after 1 h, 2 h, 5 h, 8 h, 24 h, 48 h, 3 d and 5 d and frozen at −20° C. IL-4 stimulation of HD cells resulted in a significantly increased cell size (FIGS. 6A, B and C). The number of cells that were >30 micron increased significantly from 2% before stimulation to 14% in 75 hours poststimulation.

Figure 7C:
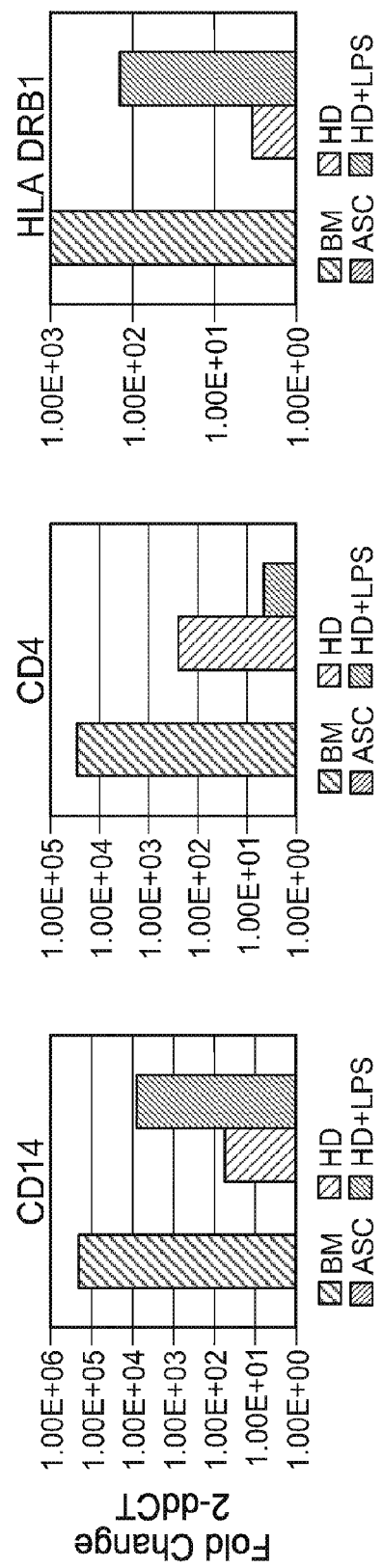

Further quantitative and real time PCR analyses revealed that IL4 stimulation caused marginal decreases in the expression of CD4 and CD8 genes in stimulated HD cells compared to un-stimulated HD cells. The expressions of macrophage specific markers such as MCP1 and CD68 were reduced by almost one-half following IL4 stimulation. On the contrary, IL-4 stimulation strongly induced the expression of HLA DRB1 in HD cells (up to 322 fold higher than unstimulated HD—FIGS. 7A and B). LPS stimulation resulted in a greater increase in the expression of HLA DRB1 (575 fold—data not shown). In addition, CD14 expression was intensified upon LPS stimulation, whereas CD4 expression abundantly reduced (3.4 fold reduction compared with unstimulated HD cells—FIG. 7C).

The time course of profile of elapsed cytokine/chemokine release in pre- and poststimulated HD cells was studied using ELISA. Cytokine production in response to IL-4 and LPS stimulation was evaluated from one hour to 5 days post-stimulation. Assays were performed using ELISA Kits (Quansys Biosciences) to screen the media of the stimulation assays for various cytokines (e.g. IL-1α, IL-2, IL-5, IL-10, IL-13, IL-17, IFNγ, TNFα and TNFβ). The chemiluminescent signal was detected using a CCD imaging system (Alpha Innotek FluoChem 8900) and finally analyzed with the Quansys Q-View™ Plus array software. HD cells appeared to exhibit an early response to LPS stimulation by increasing expression of IL-2 (~1,400 pg/ml), IL-10 (~140 pg/ml), and IL-17 (~300 pg/ml) with a peak release after 1-2 hours of stimulation. Late response (24 hours and above) to LPS stimulation was observed by increased secretion of IL-1α (~200 pg/ml) and IL-13 (~3,000 pg/ml). However, after LPS stimulation no change in expression of IL-5, TNFα, TNFβ and IFNγ was detected.

Unlike LPS, IL-4 stimulation causes an early secretion peak of IL-13 (2-5 h) reaching concentrations of ~1,500 pg/ml and a late response peak for IL-5 following 3 days of stimulation (up to ~250 pg/ml). IL-1α secretion seems to be suppressed by IL-4 (~250 pg/ml) and this stayed below the basal secretion rate in un-stimulated HD cells. However, there was a small increase in TNFα and IFNγ levels after exposure of 8 h to IL-4. The levels of IL-2, IL-10 and IL-17 secretions were not affected by IL-4 stimulation in HD. Upon IL-4 stimulation, the level of IL-17 secretion was not affected in HD cells. Un-stimulated HD cells released significant amount of IL-2 (up to ~750 pg/ml) and IL-10 (~150 pg/ml) which rapidly declined after ~8 days.

Upon stimulation with LPS, the expression of IL-2, IL-10, IL-17 and TNFβ in undifferentiated ASCs was detectable. This however was significantly lower compared to HD cells. IL-4 stimulation of undifferentiated ASCs caused increased secretion of IL-13, IL-17, and TNFα and a decrease in IL-2 expression. However, there was no detectable change in the expression in IL-1α secretion upon IL-4 or LPS stimulation of un-differentiated ASCs. Since the differentiation resulted from treatment with IL-1β and IL-4, ELISA data on these two cytokines could not be obtained. IL-6, IL-8, IL-12p70, IL-15 and IL-23 release were not convincingly detectable (data not shown).

EXAMPLE 2

Adipose tissue has been shown by the present inventors to be a viable source for the numbers of cells needed for autologous transplantation. The ADSCs of Example 1 were obtained from cohesive piece of abdominal adipose tissue to reduce the possible contamination of MSCs with CD34+ cells. Analysis of the quantities of ADSC in adipose tissue from a larger cohort of liposuction patients is exemplary of the numbers of ADSC present in adipose tissue generally as well as the differentiation potential of cells from adipose tissue. In an analysis of specimens obtained from 42 individual donors, a mean of 247,401±136,514 ADSCs were recovered from a single milliliter of liposuction effluent within a 6.0±2.4 day expansion period. Based on this recovery, collection and expansion from as little as 10 ml of liposuction effluent would provide approximately $2.4 \times 10^6$ cells, which is on par with the numbers of granulocyte-macrophage colony forming units in reinfused peripheral blood stem cells ($3.42 \times 10^4$/kg (range 3.03-18.01) PBSC) that have been used to augment autologous bone marrow transplantation (12.4×104/kg (range 4.16-28.6) ABMT). See Mitchell, P L et al. "Peripheral blood stem cells used to augment autologous bone marrow transplantation" *Arch Dis Child* 70 (1994) 237-240.

After passage in vitro, these cells, which the present inventors identified as adipose-derived stem cells, exhibited a differentiation potential comparable to that of bone marrow derived Mesenchymal Stem Cells (BMSCs). Within 2-3 passages after the initial plating of the primary culture, ADSCs appear as a monolayer of broad, flat cells (20-30 μm in diameter). By impedance sensing in a Coulter counter, such cells have a diameter of 12-18 μm after culturing for several passages. In contrast, BMSCs showed heterogeneous groups of low contrast flat cells together with smaller, more spindle-shaped cells. Self-renewal potential of ADSC and BMSC was demonstrated by single cell cultures that generated CFU (colony forming unit) clones after 2 weeks of culture.

In certain embodiments of the present invention, ADSC whether derived from cohesive pieces of adipose tissue or from lipoaspirate are further subject to clonal isolation to ensure the purity of the population.

EXAMPLE 3

In one embodiment, the adipose derived MSCs will be differentiated to hematopoietic cells using a cocktail of chemicals and cytokines. In one embodiment, the MSCs will be differentiated to myeloid lineages using the following protocol. MSCs will be expanded in growth media supplemented with 20% FBS and 100 ng/ml G-CSF for 8 days to generate neutrophils or 10 ng/ml IL-3 and 5 ng/ml IL-5 for 12-14 days to generate eosinophils. For macrophage differentiation MSCs will be plated at a density of approximately 5000 cells per cm2 in differentiation media consisting of α-MEM, 10% FBS and 0.1 μl/ml IL-monothioglycerol (MTG, Sigma-Aldrich) supplemented with 100 U/ml IL-113 (Sigma), 500 U/ml IL-3 (Prospec Bio) and 20 U/ml M-CSF (Prospec Bio) as stimulating substances. Dendritic cell differentiation will be performed in low-adherence conditions in pHEMA-coated flasks in Stemline II serum free hematopoietic stem cell expansion medium (Sigma-Aldrich) supplemented with 1% EX-CYTE (an aqueous microemulsion of bovine lipoproteins, which is isolated from bovine serum and utilized as a serum free supplement—available from the Chemicon division of Millipore) and containing 20 ng/ml GM-CSF and 20 ng/ml IL-4.

EXAMPLE 4

In one embodiment of the invention, adherent cells from human lipoaspirate are isolated and, as depicted in the flow chart of FIG. 1, are exposed to select induction media to preorient responsive cells into a desired mesenchymal differentiation track to evaluate the multilineage potential and as sources of differentiated cells for administration into a patient in need thereof. The following are non-limiting examples of induction media that are known to drive the differentiation of cells into particular lineages by prolonged culture in the media. Other combinations of differentiation factors have been shown to drive ADSC to a particular lineage. See e.g. Schaffler A, Bühler C. "Concise Review: Adipose Tissue-Derived Stromal Cells-Basic and Clinical Implications for Novel Cell-Based Therapies" *Stem Cells* 25 (2007) 818-827.

| Lineage | Component | Conc. |
| --- | --- | --- |
| Adipogenic | DMEM, low glucose | |
| | Fetal bovine serum (FBS) | 10% |
| | L-glutamine | 2 mM |
| | Penicillin/Streptomycin | |

| Lineage | Component | Conc. |
|---|---|---|
|  | L-Ascorbic acid | 100 µM |
|  | 1-methyl-3-isobutylxanthine, (IBMX) | 0.5 mM |
|  | Dexamethasone | 1 µM |
|  | Indomethacin | 100 µM |
|  | Insulin human recombinant | 10 µg/ml |

Assess subsequent adipogenesis by Oil Red O staining

| Lineage | Component | Conc. |
|---|---|---|
| Chondrogenic | DMEM, high glucose |  |
|  | FBS | 10% |
|  | Dexamethasone | 0.1 µM |
|  | Ascorbate-2-phosphate | 25 ug/ml |
|  | Insulin, bovine | 10 µg/ml |
|  | TGFβ-3 (R&D) | 10 µg/ml |
|  | Sodium pyruvate | 1 mM |
|  | Non-essential amino acids |  |
|  | Proline | 0.M |
|  | Transferrin | 5.5 µg/ml |
|  | Sodium selenite | 5 ng/ml |
|  | Linoleic Acid | 4.7 ng/ml |
|  | Bovine Serum Albumen (BSA) | 0.5 mg/ml |

Assess chondrogenesis by expression of proteoglycan or collagen II using histochemistry or immunohistochemistry staining.

| Lineage | Component | Conc. |
|---|---|---|
| Endothelial | DMEM, (low glucose) |  |
|  | FBS | 2% |
|  | Penicillin | 10 U/ml |
|  | Streptomycin | 100 ug/ml |
|  | VEGF | 50 ng/ml |
|  | L-glutamine | 2 mM |

Assess endothelial like cells by detection of vWF by Immunohistochemistry

| Lineage | Component | Conc. |
|---|---|---|
| Hepatogeneic | DMEM, (1 g/L glucose) |  |
|  | FBS | 1% |
|  | bFGF (Chemicon) | 10 ng/ml |
|  | aFGF (Chemicon) | 20 ng/ml |
|  | EGF | 10 ng/ml |
|  | HGF (R&D) | 20 ng/ml |
|  | Insulin-transferrin-selenious acid (ITSBDBiosciences) | 1% |
|  | Oncostatin M (OSM) | 10 ng/ml |

Assess hepatogenesis by detection of albumin by immunofluorescence.

| Lineage | Component | Conc. |
|---|---|---|
| Myogenic | DMEM, (low glucose) |  |
|  | FBS | 10% |
|  | Horse Serum (HS) | 5% |
|  | Penicillin/streptomycin | 1% |
|  | Hydrocortisone | 50 µM |

Assess myogenesis by detection of myosin by immunofluorescence.

| Lineage | Component | Conc. |
|---|---|---|
| Neurogenic | DMEM, F12 |  |
|  | FBS | 1% |
|  | B27 (Invitrogen) | 2% |
|  | L-ascorbic acid | 50 µM |
|  | Insulin | 5 µg/ml |
|  | bFGF (Chemicon) | 10 ng/ml |
|  | bEGF | 10 ng/ml |
|  | NGF (R&D) | 10 ng/ml |
|  | 2-mercaptoethanol | 1 mM |
|  | forskolin | 10 µM |
|  | cAMP | 2 mM |
|  | 1-methyl-3-isobutylxanthine, (IBMX) | 0.5 mM |
|  | indomethacin | 200 µM |

Assess neurogenesis by detection of microtubule-associated protein-2 (MAP-2) by immunofluorescence.

| Lineage | Component | Conc. |
|---|---|---|
| Osteogenic | FBS 10% |  |
|  | Dexamethasone | 0.1 µM |
|  | L-Ascorbic acid | 0.2 mM |
|  | β-glycerol phosphate | 10 mM |

Assess subsequent mineralization by calcium deposit by staining with Alizarin Rd S

EXAMPLE 5

In one embodiment, adipose derived MSCs will be differentiated by transferring the nuclear extracts from mixed and subset purified hematopoietic cells to the MSCs. In one embodiment, a heterogeneous population of bone marrow (BM) cells, including supporting cells, is utilized as "trainer cells." By "trainer cells" it is meant cells whose differentiation status is desired to be transferred. In certain embodiments, the adherent stromal cell subset population from the BM is utilized as the trainer cell population. Adherent stromal cells of the bone marrow constitute approximately 0.1% of the total nucleated cells of the BM.

Typically, BM is extracted in a medium containing anticoagulent and the nucleated cells are isolated, such as by centrifugation over FICOLL-HYPAQUE (Pharmacia Biotech). The nucleated cells of the BM can be used as a mixed population or can be enriched in one or more subset populations prior to isolation of nuclear extracts. In one embodiment, the BM derived "trainer cell" extracts are prepared batchwise and cryopreserved for use. One method of such cryopreservation can be found in Greenberger U.S. Pat. No. 6,991,787.

A suitable method of induced differentiation by transfection with extracts from "trainer cells" was reported by certain of the present inventors in Schimrosczyka, K. et al. "Liposomemediated transfection with extract from neonatal rat cardiomyocytes induces transdifferentiation of human adipose-derived stem cells into cardiomyocytes" *Scand J Clin Lab Invest.* 68(6) (2008) 464-72. As described, nuclear protein can be obtained from bone marrow harvested from healthy volunteer donors using the NEPER nuclear extraction reagents (Pierce, Rockford, Ill., USA). By applying this method the qualitative but also the quantitative variety and distribution of the various hematopoietic cell lines can be used for induction of respective lines in a distribution that recapitulates their relative distribution with the bone marrow.

To follow and optimize loading conditions, the extracted proteins can be labeled with a marker probe, such as by non-limiting example, fluorescein isothiocyanate (FITC) using the EZ label Fluorescein Protein labelling kit (Pierce, Rockford, Ill., USA). For protein transfection, MSCs have been successfully transfected with 3.5 mg of protein and 10 mL of transfection reagent (Pierce, Rockford, Ill., USA) and incubated for 4 h in serum-free medium. After incubation, the medium is exchanged, such as with 20% FBS-containing medium. Transfection efficiency and viability will be subsequently determined by flow cytometry. Genomic studies can be performed by microarray analysis on extracted RNA from differentiated MSCs by different methods. RNA from undifferentiated MSCs and bone marrow will serve as controls. RNA samples can be processed in triplicates for hybridization to microarray human chip and gene expression data analyzed. Probes with all samples "absent" (lower than background levels) will be removed from further analysis and differentially expressed genes will be determined in the comparison of experimental samples to baseline changes of >1.5-fold. In proteomics studies, specifically, a comparative technique can be employed using quantitative methods frequently used in proteomics such as, for example, 2D DIGE (difference gel electrophoresis), cICAT (cleavable isotope-coded affinity tags) and iTRAQ (isobaric tags for relative and absolute quantification), to precisely identify the proteins which play the most role in differentiation of MSCs. Particular subproteome, membrane, cytosolic, or nuclear factors which are major elements in differentiation of MSCs will be identified thus enabling identification of therapeutic target and diagnostic markers.

EXAMPLE 6

In one embodiment of the invention, MSCs isolated from adipose tissue will be differentiated into hematopoietic cells by co-culture system with bone marrow derived cells functioning as trainer cells. Although bone marrow cells must be collected for co-culture, the ability to differentiate adipose derived MSC by co-culture provides a mechanism to greatly increase the numbers of cells ultimately available for transplantation without having to harvest the entire cell quantity from the bone marrow. Thus, in one embodiment a modest number of BM cells taken from a single harvest site of a healthy allogenic donor are used to direct maturation of MSC derived from readily available adipose tissue of the patient. In other embodiments, a relatively modest collection of autologous bone marrow is obtained from the patient and used as trainer cells. The optimum ratio of MSC/hematopoietic cells will be identified using ASCs and cultures of CD45+, CD34+, CD133+ cells obtained from bone marrow. The cell proliferation and immunophenotypic differentiation of derived MSCs will be assessed. In certain embodiments, particularly with autologous transplantation where there is a concern that the transplant may be contaminated with abnormal cells, the adipose derived stem cells of the patient are separated from any malignant or otherwise abnormal cells and precursors thereof. Where the abnormal cells are believed to have a particular phenotype such as for instance CD34 positivity, cells bearing the particular phenotype can be removed by negative selection. Thus, for example, the trainer cells from the patient's bone marrow that may be contaminated with abnormal cells bearing CD34, the bone marrow cells are subject to removal of CD34+ cells by negative selection. In other embodiments, the trainer cells from the bone marrow are lethally irradiated prior to co-culture such that any contaminating abnormal cells cannot proliferate if transplanted into the patient.

As previously discussed, adipose derived cells are believed to have an ability to support the survival of sublethally irradiated bone marrow cells in mice if transplanted soon enough. Typical bone marrow transplantation protocols call for transplantation of bone marrow within 1-2 days after the completion of the several days of chemotherapy and/or radiation conditioning treatment. However, in one embodiment disclosed herein, in order to avoid potential support and rescue of potentially malignant residual cancer stem cells, the patient is subject to an extended postconditioning period following the chemotherapy and/or radiation and before the SVF derived stem cells are transplanted.

EXAMPLE 7

In one example, the SVF cell population is isolated as follows. Lipoaspirate is collected under informed consent in the operating room directly into a unitary purification apparatus by standard suction assisted lipoplasty with tumescent. The digestion chamber of the apparatus included a predigestion chamber and an inner postdigestion chamber separated by a nylon mesh having a pore size of approximately 1 mm. The tumescent is drained and a volume of approximately 100 ml of drained lipoaspirate is washed by draining the predigestion chamber and refilling with a solution of lactated Ringer's solution, which is prewarmed to 37° C. containing a proteolytic enzyme combination comprised of collagenase IV (60,000 U) and dispase (120 U).

A digestion recirculation loop is implemented by a pump actuated flow path from the predigestion chamber into the postdigestion chamber and including passage across a heat exchanger that maintains the digestion mixture at approximately 37° C. Recirculation is continued for approximately 30 to about 60 minutes or until greater than 90% of the cellular volume of the predigestion chamber is able to pass the 1 mm mesh into the post digestion chamber. The design of the pre and post digestion chambers, separated by the nylon mesh across which the recirculation flow path passes repeatedly, provides trapping of connective and other debris tissue on the digestion mesh. After digestion is sufficiently complete, the digestion mixture is pumped tangentially over a nylon dispersing filter having a pore size of 250 µm. The filtered digestion mixture is then pumped into a columnar lipid separating chamber that is integral to the apparatus. The filtered digestion mixture enters the lipid separating chamber through a dispersing head having a plurality of downwardly directed pores with a pore size of 500 µm and disposed proximally to a bottom inner surface of the lipid separating unit. The design is adapted for forcibly flowing the cell mixture against an inner surface within the lipid separating unit and thereby further disrupting cell clusters within the cell mixture prior to fluid phase separation. The lipid separating chamber is prefilled with a volume of 150 ml lactated Ringer's solution prior to introduction of the digestion mixture such that when the filtered digestion mixture enters the chamber, any clusters of cells, including lipids or adipocytes, are subject to fluid shear as the lipid moieties float upward in the aqueous solution. Fluid phase separation is allowed to proceed at room temperature for about 5 to about 30 minutes prior to collection of the stromal vascular fraction from the bottom of the lipid separating chamber. The SVF cells are then subject to hematopoietic differentiation conditions.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements. The method of discriminating malignant hematopoietic cells, and to use the MSC's for bone marrow transplantation.

We claim:

1. A process of generating a population of cells for hematopoietic cell transplantation comprising:
   collecting a volume of adipose tissue from a mammal and cleaning non-tissue bound circulating cells from the tissue;
   isolating stromal vascular fraction (SVF) cells from the cleaned adipose tissue, said SVF cells isolated by enzymatically digesting the cleaned adipose tissue and removing lipid containing cells;
   expanding the SVF cells in vitro to generate a population of Adipose-derived Stem Cells (ADSC) that are CD34−;
   culturing the CD34− ADSC in a hematopoietic differentiation media that promotes differentiation to a hematopoietic lineage comprising one or more differentiation factors selected from the group consisting of IL-1β, IL-3, IL-4, IL-5, G-CSF, MCSF and GM-CSF; and
   collecting the cultured cells for transplantation.

2. The process of claim 1, further comprising exposing the SVF cells to plastic adherence wherein nonadherent cells are discarded prior to expanding the SVF cells in vitro to generate the population of CD34− ADSC.

3. The process of claim 1, wherein negative selection is applied to insure essentially complete removal of any residual CD34+ cells from the CD34− ADSC prior to culture in the hematopoietic differentiation media.

4. The process of claim 1, wherein the hematopoietic differentiation media promotes differentiation into neutrophils and includes G-CSF.

5. A process of generating a population of cells for hematopoietic cell transplantation comprising:
   collecting a volume of adipose tissue from a mammal and cleaning non-tissue bound circulating cells from the tissue;
   isolating stromal vascular fraction (SVF) cells from the cleaned adipose tissue, said SVF cells isolated by enzymatically digesting the cleaned adipose tissue and removing lipid containing cells;
   expanding the SVF cells in vitro to generate a population of Adipose-derived Stem Cells (ADSC) that are CD34−;
   culturing the CD34− ADSC in a hematopoietic differentiation media that promotes differentiation into macrophages and includes IL-1β, IL-3, and M-CSF; and
   collecting the cultured cells for transplantation.

6. The process of claim 5, wherein the hematopoietic differentiation media further comprises 1-monothioglycerol (1-MTG).

7. A process of generating a population of cells for hematopoietic cell transplantation comprising:
   collecting a volume of adipose tissue from a mammal and cleaning non-tissue bound circulating cells from the tissue;
   isolating stromal vascular fraction (SVF) cells from the cleaned adipose tissue, said SVF cells isolated by enzymatically digesting the cleaned adipose tissue and removing lipid containing cells;
   expanding the SVF cells in vitro to generate a population of Adipose-derived Stem Cells (ADSC) that are CD34−;
   culturing the CD34− ADSC in a hematopoietic differentiation media that promotes differentiation into eosinophils and includes IL-3 and IL-5; and
   collecting the cultured cells for transplantation.

8. A process of generating a population of cells for hematopoietic cell transplantation comprising:
   collecting a volume of adipose tissue from a mammal and cleaning non-tissue bound circulating cells from the tissue;
   isolating stromal vascular fraction (SVF) cells from the cleaned adipose tissue, said SVF cells isolated by enzymatically digesting the cleaned adipose tissue and removing lipid containing cells;
   expanding the SVF cells in vitro to generate a population of Adipose-derived Stem Cells (ADSC) that are CD34−;
   culturing the CD34− ADSC in a hematopoietic differentiation media that promotes differentiation into dendritic cells and includes GM-CSF and IL-4; and
   collecting the cultured cells for transplantation.

9. A method of autologous stem cell transplantation comprising:
   preparing a population of autologous stem cells from a patient by a procedure comprising the steps of:
      removing a portion of adipose tissue from a patient and thoroughly washing the portion to remove non-tissue bound circulating cells prior to isolating a stromal vascular fraction (SVF) of cells from the washed adipose tissue;
      expanding the SVF cells in vitro to generate a population of Adipose-derived Stem Cells (ADSC) that are CD34−;
      culturing the CD34− ADSC in a differentiation media that comprises at least one differentiation factor selected from the group consisting of IL-1β, IL-3, IL-4, IL-5, G-CSF, MCSF, and GM-CSF;
      collecting and storing the cultured cells until transplantation;
      conditioning the patient by chemotherapy and/or radiation to destroy abnormal stem cells and blood cells;
      isolating the patient for an extended post-conditioning period; and
      transplanting the cultured cells into the patient.

10. The method of claim 9, further comprising a step of exposing the SVF cells to plastic adherence wherein nonadherent cells are discarded prior to expanding the SVF cells in vitro to generate the population of CD34− ADSC .

11. The method of claim 9, wherein negative selection is applied to insure essentially complete removal of any residual CD34+ cells from the CD34− ADSC prior to culture in the differentiation media.

12. The method of claim 9, further comprising:
    isolating a quantity of cancer-free autologous or allogeneic bone marrow trainer cells; and
    co-culturing the bone marrow trainer cells with the SVF cells.

13. The method of claim 12, wherein the cancer-free bone marrow trainer cells are mixed population of nucleated cells representing a respective distribution of hematopoietic lineages in the bone marrow.

14. The method of claim 12, wherein the cancer-free bone marrow trainer cells are purified into subsets of cells and the subsets are co-cultured with the SVF.

15. The method of claim 12, further comprising removing CD34+ cells from the SVF cells prior to co-culture.

16. The method of claim 12, wherein the cancer-free bone marrow trainer cells have been treated by removal of CD34+ cells prior to co-culture.

17. The method of claim 12, wherein the cancer-free bone marrow trainer cells have been treated by lethally irradiating the bone marrow trainer cells to render them cancer free prior to the co-culture.

\* \* \* \* \*